(12) United States Patent
Brunelle et al.

(10) Patent No.: US 9,566,368 B2
(45) Date of Patent: Feb. 14, 2017

(54) MOLDABLE BONE GRAFT COMPOSITIONS

(71) Applicant: BioStructures, LLC, Newport Beach, CA (US)

(72) Inventors: John E. Brunelle, Huntington Beach, CA (US); Russell L. Cook, Newport Beach, CA (US); Duraid S. Antone, Laguna Niguel, CA (US)

(73) Assignee: Bioventus, LLC, Durham, NC (US)

( * ) Notice: Subject to any disclaimer, the term of this patent is extended or adjusted under 35 U.S.C. 154(b) by 0 days.

(21) Appl. No.: 14/939,902

(22) Filed: Nov. 12, 2015

(65) Prior Publication Data

US 2016/0136325 A1  May 19, 2016

Related U.S. Application Data

(60) Provisional application No. 62/079,047, filed on Nov. 13, 2014.

(51) Int. Cl.
*A61L 27/12* (2006.01)
*A61L 27/18* (2006.01)
*A61L 27/50* (2006.01)
*A61L 27/54* (2006.01)
*A61L 27/58* (2006.01)
*A61L 27/46* (2006.01)

(52) U.S. Cl.
CPC ............... *A61L 27/58* (2013.01); *A61L 27/46* (2013.01); *A61L 2430/02* (2013.01)

(58) Field of Classification Search
CPC ............ A61L 2300/112; A61L 2300/40; A61L 2300/404; A61L 2400/06; A61L 2430/02; A61L 27/12; A61L 27/18; A61L 27/3608; A61L 27/50; A61L 27/54; A61L 27/58
See application file for complete search history.

(56) References Cited

U.S. PATENT DOCUMENTS 5,468,544 A * 11/1995 Marcolongo ........... A61F 2/367
                                                        428/373
6,228,386 B1   5/2001 Yang
8,785,513 B2 *  7/2014 Lassila ................. A61K 6/0023
                                                        433/228.1

FOREIGN PATENT DOCUMENTS

WO    WO 2007068489    *  6/2007   ............. A61L 27/12

OTHER PUBLICATIONS

Lai et al. (Advanced Materials Research. 2013; 622-623:1794-1798; online Dec. 27, 2012).*
Betz, Randal R. "Limitations of autograft and allograft: new synthetic solutions." Orthopedics (2002); 25(5): S561-S570.
Boden et al. "An Experimental Lumbar Intertransverse Process Spinal Fusion Model: Radiographic, Histologic, and Biomechanical Healing Characteristics." Spine (1995); 20(4): 412-420.
Daculsi et al. "Current state of the art of biphasic calcium phosphate bioceramics." Journal of Materials Science: Materials in Medicine (2003); 14(3): 195-200.

(Continued)

*Primary Examiner* — Ernst V Arnold
(74) *Attorney, Agent, or Firm* — Cooley LLP

(57) ABSTRACT

The present disclosure relates to compositions useful in synthetic bone graft applications. Particularly, the disclosure teaches moldable bone graft compositions, methods of making said compositions, and methods of utilizing the same.

48 Claims, 13 Drawing Sheets

(56) References Cited

OTHER PUBLICATIONS

Erulkar et al. "Flexibility analysis of posterolateral fusions in a New Zealand white rabbit model." Spine (2001); 26(10): 1125-1130.
Fellah et al. "Osteogenicity of biphasic calcium phosphate ceramics and bone autograft in a goat model." Biomaterials (2008); 29(9): 1177-1188.
Garrido et al. "Biphasic calcium phosphate bioceramics for orthopaedic reconstructions: clinical outcomes." International Journal of Biomaterials (2011), Article IDS 129727, 9 pages.
Hing, et al. "Comparative performance of three ceramic bone graft substitutes." The Spine Journal (2007); 7(4): 475-490.
Kang et al. "Grafton and local bone have comparable outcomes to iliac crest bone in instrumented single-level lumbar fusions." Spine (2012); 37(12): 1083-1091.
LeGeros et al. "Biphasic calcium phosphate bioceramics: preparation, properties and applications." Journal of Materials Science: Materials in Medicine (2003); 14(3): 201-209.
Schepers and Ducheyne. "Bioactive glass particles of narrow size range for the treatment of oral bone defects: a 1-24 month experiment with several materials and particle sizes and size ranges." Journal of Oral Rehabilitation (1997); 24(3): 171-181.
Szpalski and Gunzburg. "Applications of calcium phosphate-based cancellous bone void fillers in trauma surgery." Orthopedics (2002); 25(5): S601-S609.
Vaccaro, Alexander R. "The role of the osteoconductive scaffold in synthetic bone graft." Orthopedics (2002); 25(5): S571-S578.
Xie et al. "Evaluation of the osteogenesis and biodegradation of porous biphasic ceramic in the human spine." Biomaterials (2006); 27(13): 2761-2767.

\* cited by examiner

MOLDABLE BONE GRAFT COMPOSITIONS

CROSS-REFERENCE TO RELATED APPLICATIONS

The present application claims the benefit of priority to U.S. Provisional Patent Application No. 62/079,047, filed on Nov. 13, 2014, which is hereby incorporated by reference in its entirety for all purposes.

FIELD

The present disclosure relates to compositions useful in synthetic bone graft applications. Particularly, the disclosure teaches moldable bone graft compositions, methods of making said compositions, and methods of utilizing the same.

BACKGROUND

Current bone grafting procedures include the use of autogenous bone as a graft material (i.e., "autografting"). Use of autogenous bone, however, subjects a patient to increased pain and discomfort, and an increased risk of infection, because it requires the patient to undergo additional surgery to recover the autogenous bone for use in the grafting procedure.

Current bone grafting also includes the use of bone from a donor as a graft material (e.g., "allografting" from the same species or "xenografting" from a different species). Both allograft bone and xenograft bone, though from natural sources, subject a patient to the risk of disease transmission and graft rejection.

A third option in the field of bone grafting includes the use of synthetic bone graft material. Some synthetic bone graft material is mixed with autograft, allograft, or xenograft bone, and thus still subjects a patient to the risks above. Other disadvantages to current synthetic bone graft materials are: (1) the poor resorbability profile of many synthetic bone graft compositions, which leads to low proliferation and remodeling of new bone throughout the defect site, (2) low bioactivity or other osteogenic effects, (3) the inability to mold or form the material into a desirable shape during intraoperative surgical procedures, (4) the inability to maintain the desired placement at the defect site, (5) lack of antimicrobial properties, and (6) the inability to combine bone healing properties of different synthetic materials into a single implant.

As such, there is a great need in the art for an improved synthetic bone graft material that is moldable, highly bioactive, and presents an optimal resorbability profile that increases the proliferation and remodeling of new bone throughout a defect site.

SUMMARY OF THE DISCLOSURE

The present disclosure addresses the need in the medical community of a superior synthetic bone graft material, by providing a moldable bone graft composition that is: (1) moldable, to facilitate surgeon handling and maintain placement of granules at the defect site; (2) bioactive, to initiate immediate apatite layer formation and facilitate proliferation and remodeling of new bone throughout the defect site; (3) osteostimulative, to stimulate the proliferation and differentiation of bone healing cells, (4) anti-microbial, to inactivate infectious agents common to surgical procedures, and (5) provides a gradual resorption profile between the soluble, faster resorbing β-TCP, and more stable, slower resorbing HA, in an optimized ratio in line with the host remodeling process. The combination of bioactive glass, biphasic mineral, and resorbable polymer carrier addresses the intraoperative handling needs of the surgeon, as well as the long and short term healing demands of for example, spine fusion procedures.

In aspects, the moldable bone graft composition of the present invention is a bone void filler composition, which can optionally be loaded into a device for filling bony voids or gaps of the skeletal system, and can be used in conjunction with autograft as a bone graft extender. The bone void filler of the present invention can be resorbed and replaced with host bone during the healing process.

In an aspect, the disclosure provides for a moldable bone graft composition, comprising: about 40-80% by weight of one or more bioresorbable polymers; about 10-50% by weight of biphasic calcium phosphate particles comprising hydroxyapatite (HA) and beta-tricalcium phosphate (β-TCP); and about 1-40% by weight of at least one bioactive glass, wherein said calcium phosphate particles and said bioactive glass together comprise about 20-60% by weight of the moldable bone graft composition.

In a particular aspect, the one or more bioresorbable polymers comprise a polyalkylene oxide polymer having a molecular weight of about 500-1500 grams/mole, a specific gravity of about 1.0-1.3 (at 25° C.), and a viscosity of about 10-40 cSt (at 210° C.) using methods described in the USP-NF monograph for Polyethylene Glycol. In this aspect, the polymer has a melting temperature of about 38-50° C. measured by differential scanning calorimetry.

In a particular aspect the alkylene oxide polymer is comprised of a blend of USP-NF grades of PEG 1450 and PEG 400, in a weight ratio of about 75:25 to 85:15.

In one aspect, the moldable bone graft compositions taught herein comprise biphasic HA/β-TCP particles that contain about 20-60% hydroxyapatite and about 40-80% β-tricalcium phosphate.

In some aspects, the moldable bone graft compositions taught herein comprise biphasic HA/β-TCP particles that contain about 60% hydroxyapatite and about 40% β-tricalcium phosphate.

In embodiments, the moldable bone graft compositions comprise calcium phosphate particles that have interconnected macro- and microporosity.

In some embodiments, the moldable bone graft composition comprising calcium phosphate particles has about 30-90% of the calcium phosphate particles with a diameter of about 1000-2000 μm; about 10-70% of the calcium phosphate particles with a diameter of about 425-1000 μm, about 10-50% of the calcium phosphate particles with a diameter of about 710-1000 and about 1-30% of the calcium phosphate particles with a diameter of about 425-710 μm.

In embodiments, the moldable bone graft composition comprises 45S5 bioactive glass. In embodiments, the bioactive glass is in the form of particles having a diameter of about 1-600 μm. In embodiments, the bioactive glass is in the form of particles having a diameter of about 1-425 μm. In embodiments, at least 60%, or 70%, or 80%, or 90%, or 95% of the bioactive glass is in the form of particles having a diameter of about 212-420 μm.

In aspects, the bioactive glass is in the form of irregular granules. In other aspects, the bioactive glass is in the form of approximately spherical particles. In yet other aspects, the bioactive glass is in the form of fibers.

In an embodiment, the moldable bone graft composition comprises calcium phosphate particles and bioactive glass, along with an alkylene oxide polymer carrier, and about 60-90% of the calcium phosphate particles and bioactive glass together are in the form of particles having a diameter of about 425-2000 μm, and about 10-40% of the particles have a diameter of about 1-425 μm.

In certain aspects, the moldable bone graft composition is formulated as a single use composition having a mass of about 1.5 grams to about 30 grams.

In some aspects, the moldable bone graft composition is in the form of a single use composition. In some aspects, the single use moldable bone graft composition has a volume of about 1-20 cc.

In certain aspects, the moldable bone graft composition has a density of about 1.2-1.8 g/cc.

In embodiments, the moldable bone graft composition is in the form of a cylinder. In other aspects, the moldable bone graft composition is in the form of a cubical shape.

In embodiments, the moldable bone graft composition has a crush resistance force of less than about 20 lbf, and a crush resistance stiffness of less than about 90 lbf/in, using a hand-held force gage with a one-half inch platen. The device was tested in its final commercial form, approximately 15 grams of material, 0.62 inches in diameter and 2.0 inches in length. The force gage platen was placed applied perpendicular to the long axis of the implant.

In embodiments, the moldable bone graft composition can be molded into any desired shape without loss of homogeneity.

In aspects, a syringe applicator can be filled with the moldable bone graft composition, in order to facilitate application of the composition. In certain aspects, the force required to eject the moldable bone graft composition from the syringe applicator is less than 20 lbf using a hand held force gage with a one-half inch platen and simulated use conditions, where the platen is applied to the pushrod of the syringe applicator to forcibly eject the bone graft from the syringe. The device was tested in its final commercial form, 15 grams of material, 0.62 inches in diameter and 2.0 inches in length, loaded into a 0.62 inch open barrel syringe.

In certain embodiments, the moldable bone graft compositions taught herein further comprise a melt skin layer disposed on the outer surface of the composition, wherein the melt skin layer comprises a bioresorbable polymer. In aspects, the melt skin serves to facilitate ejection from the syringe and enhance the cosmetic appearance of the implant.

In embodiments, the moldable bone graft composition comprises a bioresorbable polymer that dissolves in phosphate buffered saline (PBS) at 37° C. at a rate of about 0.01-0.20 grams/minute, determined by placing 15 grams of bone graft material in an ASTM E-11 45 micron sieve, submerging in 500 ml of circulating PBS, and measuring mass loss at 7.5, 15, 30, 45 and 60 minutes.

In embodiments, the moldable bone graft composition comprises a bioresorbable polymer that dissolves in PBS at 37° C. in about 60-600 minutes, determined by placing 15 grams of bone graft material in an ASTM E-11 45 micron sieve, submerging in 500 ml of circulating PBS, and measuring mass loss at 7.5, 15, 30, 45, 60 and 600 minutes.

In embodiments, the moldable bone graft composition comprises a bioresorbable polymer that dissolves in PBS at 37° C. in less than 60 minutes, determined by placing 15 grams of bone graft material in an ASTM E-11 45 micron sieve, submerging in 500 ml of circulating PBS, and measuring mass loss at 7.5, 15, 30, 45 and 60 minutes.

In aspects, the disclosure teaches a moldable bone graft composition, comprising: about 50-70% by weight of one or more bioresorbable polymers; about 25-40% by weight of biphasic calcium phosphate particles comprising a blend of hydroxyapatite and tricalcium phosphate; and about 1-15% by weight of at least one bioactive glass, wherein said calcium phosphate particles and said bioactive glass together comprise about 30-50% by weight of the moldable bone graft composition.

In embodiments, the moldable bone graft compositions taught herein form a hydroxyapatite surface layer in simulated body fluid (SBF).

In embodiments, the moldable bone graft compositions taught herein stimulate mesenchymal stem cell differentiation in MG63 osteosarcoma and C2C12 mesenchymal cell lines.

In embodiments, the moldable bone graft compositions taught herein stimulate osteoblast cell proliferation in MG63 osteosarcoma and C2C12 mesenchymal cell lines.

In embodiments, the moldable bone graft compositions taught herein demonstrate antimicrobial efficacy according to methods based on USP <51> Antimicrobial Effectiveness Test.

In embodiments, the moldable bone graft compositions taught herein provide a spine fusion rate of greater than 50% in a New Zealand white rabbit spine fusion model, as determined by radiographic analysis, manual palpation analysis and biomechanical analysis.

In embodiments, the moldable bone graft compositions taught herein provide a spine fusion rate of at least about 80% in a New Zealand white rabbit spine fusion model, as determined by biomechanical range of motion analysis in flexion-extension.

In embodiments, the moldable bone graft compositions taught herein can be used in a method to repair a bone defect. In aspects, the method comprises applying the moldable bone graft composition to a bone defect in a patient in need thereof. In some embodiments, the defect is a spinal bone defect. In some aspects, the bone defect is in the posterolateral gutter of a vertebral body.

In an embodiment, the moldable bone graft composition is bioactive. In another embodiment, the bioactive moldable bone graft composition comprises a biphasic mineral granulate of HA/β-TCP particles (1-2 mm) and bioactive glass (212-420 μm), which are suspended in an alkylene oxide polymer carrier. In certain aspects, the aforementioned moldable bone graft composition is formulated as putty. In some embodiments, the aforementioned moldable bone graft composition exhibits synergistic effects, which are greater than the additive effects that one would encounter utilizing biphasic HA/β-TCP based granulate or bioactive glass particles alone. For example, the 45S5 bioactive glass particles, homogeneously dispersed between the biphasic mineral granulate, elicit an immediate and robust bioactive response, resulting in apatite layer formation and bone cell attachment on the bioactive glass surface. This response results in a more rapid recruitment and infiltration of bone healing cells within the biphasic mineral granulate matrix, thus accelerating and enhancing its own osteoconductive response. In addition, the initial bioactive response of the faster resorbing bioactive glass particles is supported and perpetuated by the more gradual resorbing biphasic granulate. Thus, the presence of bone healing elements due to the bioactive glass dispersed among the biphasic results in more rapid osteoconductivity and remodeling than would occur with the biphasic granules alone.

In aspects, the moldable bone graft composition is optimized for bone remodeling in posterolateral spine fusion procedures. In aspects, the moldable bone graft compositions taught herein exhibit a gradual resorption rate, porosity, and microstructure, which result in a stable scaffold that allows sustained osteoconductivity during the healing process.

The moldable bone graft compositions of the present disclosure, in certain aspects, are a synthetic bone void filler device comprised of biphasic HA/β-TCP (60:40) calcium phosphate granules & 45S5 bioactive glass particles suspended in a resorbable alkylene oxide polymer (AOP) carrier. In aspects, the moldable carrier allows the surgeon to shape and apply the implant based on each patient's unique anatomy, and serves to maintain the placement of implant materials at the defect site until closure. Once implanted, the biocompatible, resorbable polymer carrier is excreted from the body through natural metabolic pathways. In particular applications, after implantation of the moldable bone graft compositions, the 45S5 bioactive glass component undergoes a unique surface modification within the physiological environment that allows for direct bonding with surrounding bone through an exchange of biologically active ions, which produces a bioactive hydroxy carbonate apatite (HCA) layer to which bone can readily bond to. These surface reactions are followed by the proliferation and differentiation of bone related cells on the apatite matrix as part of the normal healing process.

In embodiments, the biphasic mineral granules (1-2 mm) of the present compositions, combine the long term stability of slower resorbing hydroxyapatite (HA) with the solubility of faster resorbing beta-tricalcium phosphate (β-TCP), in a ratio which the present inventors have found to provide controlled implant resorption, resulting in more reliable bone remodeling at the defect site. Dissolution of the disclosed biphasic mineral in biological fluids produces a direct bonding interface with host bone through the release of calcium and phosphate ions and subsequent formation of a surface apatite layer similar to bone mineral. In addition, the structural microporosity and macroporosity of the disclosed biphasic granules are in the optimal ranges needed to allow penetration of biological fluids (>10 μm) and support osteoconductivity (>100 μm), providing a more sustained remodeling response at the defect site.

In embodiments, the disclosure provides bioactive bone graft putty that is a bone void filler intended for use in bony voids or gaps, including those that are not intrinsic to the stability of the bony structure. These defects may be surgically created osseous defects or osseous defects created from traumatic injury to the bone. In some embodiments, the bioactive bone graft putty may be packed gently into bony voids or gaps of the skeletal system (i.e., extremities, pelvis, and posterolateral spine fusion procedures). In some embodiments, the bioactive bone graft putty can also be used with autograft as a bone graft extender in the posterolateral spine. In embodiments, the bioactive bone graft putty device provides bone void filler that is resorbed and replaced with host bone during the healing process.

In embodiments, the disclosure provide a bioactive bone graft putty that is a synthetic bone void filler comprised of a blend of calcium phosphate materials (e.g., biphasic calcium phosphate granules comprising hydroxyapatite and tricalcium phosphate) and bioactive glass granules suspended in a resorbable polymer carrier that facilitates handling and delivery of the granule components. In embodiments, the device is supplied as putty, pre-loaded in a syringe applicator, and packaged in a sterile barrier foil pouch or blister tray. In embodiments, the device is provided sterile, for single use, in a variety of sizes.

The moldable bone graft compositions of the present disclosure may be supplied with, or used in conjunction with, allograft tissue. Thus, in aspects, the moldable bone graft compositions taught herein comprise allograft tissue. In other aspects, a physician may add the allograft tissue at the point of care in conjunction with the moldable bone graft compositions taught herein.

DETAILED DESCRIPTION

Figure 1A:
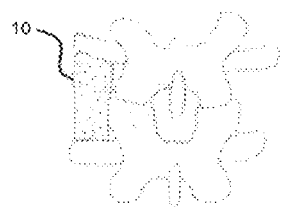
FIG. 1A is a posterior view of a bone graft composition according to an embodiment implanted between transverse processes of vertebra.

Compositions, materials, methods, and kits for bone grafting, including for repairing and/or filling a void or gap in a bone or other bony structure of a patient, are described herein. Also described herein are methods for preparing such compositions and materials.

DEFINITIONS

As used in this specification, the singular forms "a," "an" and "the" include plural referents unless the context clearly dictates otherwise. Thus, for example, the term "a material" is intended to mean one or more materials, or a combination thereof.

As used herein, the term "biocompatible" refers to the ability (e.g., of a composition or material) to perform with an appropriate host response in a specific application, or at least to perform without having a toxic or otherwise deleterious effect on a biological system of the host, locally or systemically.

As used herein, the term "osteoconductive" refers to the ability (e.g., of a composition or material) to passively permit bone growth (e.g., onto and/or into the material). As such, osteoconduction can be characterized as a passive process.

A material (e.g., a graft or implant) can be osteoconductive, for example, because it is configured to passively permit growth of bone on a surface of the material. In another example, a material can be osteoconductive, because it is configured to passively permit growth of bone into an opening (e.g., a pore) of the material.

As used herein, the term "osteoinductive" refers to the capability (e.g., of a composition or material) to actively stimulate a biological response which induces bone formation. As such, osteoinduction can be characterized as an active process.

Osteoinduction can include the formation and/or stimulation of osteoprogenitor cells, such as osteoprogenitor cells in bodily tissue surrounding or proximate to a graft or implant.

As used herein, the term "bioactive" refers to the capability (e.g., of a composition or material) to form a hydroxyapatite (HA) surface layer when immersed in simulated body fluid (SBF)

As used herein, the term "osteostimulative" refers to the capability (e.g., of a composition, material, or extract thereof) to enhance or actively stimulate proliferation of osteoblasts and differentiation of mesenchymal stem cells.

As used herein, the term "anti-bacterial" or "anti-microbial" refers to the capability (e.g., of a composition, materials, or extract thereof) to inhibit the growth of microorganisms based on methods described in USP <51>.

As used herein, the term "biodegradable" refers to the capability of a material to be degraded, disassembled, and/or digested over time by action of a biological environment (including the action of living organisms, e.g., the patient's body) and/or in response to a change in physiological pH or temperature. Biodegradable, in the context of a human body environment, implies that the material is degraded, disassembled, and/or digested under normal physiological conditions.

As used herein, the terms "resorbable" and "bioresorbable" refers to the capability of a material to be broken down over a period of time and assimilated into the biological environment. Resorbable and bioresorbable, in the context of a human body environment, implies that the material is broken down over a period of time and assimilated into the body under normal physiological conditions.

As used herein, the term "moldable" refers to the property of being pliable, able to be compressed, shaped, and manipulated by force of hand, while maintaining integrity, homogeneity of the composition, physical properties, and performance properties.

As used herein, references to a weight of components of a bone graft composition or material described herein, such as the phrase "by weight," refer to the weight of the applicable component prior to being added to or mixed with another different component of the bone graft composition. For example, the weight can refer to an initial weight of the component measured out before further processing of the component into the bone graft composition.

As used herein, the phrase "non-load bearing application" refers to an application for repair of a void or gap in a bone or another bony structure in which the void or gap to be repaired is not intrinsic to the stability of the bone or bony structure.

A bone graft composition, or material, according to an embodiment facilitates repair or regeneration of bone at a target repair site. For example, in some embodiments, the bone graft composition can be osteoconductive, osteoinductive, bioactive, osteostimulative, antibacterial or any combination thereof. The target repair site can be, for example, a void, gap, or other defect in a bone or other bony structure in a body of a patient. For example, as described in more detail below, the bone graft composition facilitates bone growth at a target repair site in the spine, pelvis, an extremity, the cranium, or another bone or bony structure in the patient's body. The bone graft composition can be implanted or otherwise disposed or molded at the target repair site. For example, in some embodiments, the bone graft composition can be implanted or disposed at the target repair site in a non-load bearing application.

Bioresorbable Polymers

In embodiments, the bioresorbable polymers utilized in the disclosure are alkylene oxide polymers (AOP).

The alkylene oxide polymers, alternatively referred to as poly(alkylene oxide)s, are linear or branched-chain polymers (including homopolymers, copolymers, and graft copolymers) that contain ether linkages in their main polymer chain structure and are derived from monomers that are vicinal cyclic oxides, or epoxides, of aliphatic olefins, such as ethylene and propylene and, to some extent, butylene.

The alkylene oxide polymers of the present invention may have a range of suitable molecular weights. Lower molecular weight alkylene oxide polymers are generally liquids, increasing in viscosity with molecular weight. High molecular weight alkylene oxide polymers can be thermoplastic. The solubilities of alkylene oxide polymers range from hydrophilic water soluble polymers that are principally derived from ethylene oxide, to hydrophobic, oil-soluble polymers of propylene oxide and butylene oxide.

In embodiments, the polymer carrier comprises a polyethylene glycol or "PEG" polymer, which is an addition polymer of ethylene oxide and water, represented by the formula $H(OCH_2CH_2)_nOH$, in which n represents the average number of oxyethylene groups.

The structure of polyethylene glycol can be represented as follows:

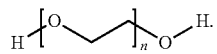

In particular aspects, the polymer utilized in the moldable bone graft compositions is one or more of a bioresorbable polymer comprising a polyalkylene oxide polymer having a molecular weight of about 500-1500 grams/mole, a specific gravity of about 1.0-1.3 (at 25° C.), a viscosity of about 10-40 cSt (at 210° C.), and a melting temperature of about 35-50° C.

In embodiments, the polymer carrier is a combination of: 1) USP-NF PEG 1450-80% wt/wt; and 2) USP-NF PEG 400-20% wt/wt. In some aspects, this property range may also be achieved using USP-NF PEG 1000. In an embodiment, the polymer carrier has the following properties, per USP testing: MW=983, Viscosity=19.0 cST (@210° F.), and a Tm=44-46° C.

In embodiments, the polymer carrier is a combination of: 1) USP-NF PEG 1450 in a range of about 50% to about 99% wt/wt; and 2) USP-NF PEG 400 in a range of about 1% to about 50% wt./wt.

In embodiments, the polymer carrier is a combination of: 1) USP-NF PEG 1450 in a range of about 60% to about 90% wt/wt; and 2) USP-NF PEG 400 in a range of about 10% to about 40% wt/wt.

In embodiments, the polymer carrier is a combination of: 1) USP-NF PEG 1450 in a range of about 70% to about 90% wt/wt; and 2) USP-NF PEG 400 in a range of about 10% to about 30% wt/wt.

In embodiments, the polymer carrier is a combination of: 1) USP-NF PEG 1450 in a range of about 75% to about 85% wt/wt; and 2) USP-NF PEG 400 in a range of about 15% to about 25% wt./wt.

In embodiments, the polymer carrier is a combination of: 1) USP-NF PEG 1450 in a concentration of about 80% wt/wt; and 2) USP-NF PEG 400 in a concentration of about 20% wt/wt.

In embodiments, the polymer carrier is a combination of: 1) USP-NF PEG 1450 in a concentration of 80%±5% wt/wt; and 2) USP-NF PEG 400 in a concentration of 20%±5% wt/wt.

In embodiments, the polymer carrier is a combination of: 1) USP-NF PEG 1450 in a concentration of 80%±2% wt/wt; and 2) USP-NF PEG 400 in a concentration of 20%±2% wt/wt.

In embodiments, the polymer carrier is a combination of: 1) USP-NF PEG 1450 in a concentration of 80%±1% wt/wt; and 2) USP-NF PEG 400 in a concentration of 20%±1% wt/wt.

Bioactive Glass

The bioactive glass of the bone graft composition facilitates the regrowth of bone at the target repair site.

In some embodiments, the bioactive glass of the bone graft composition can be an osteoconductive agent. The bioactive glass can be disposed on, embedded within, suspended within, and/or otherwise mixed with the alkylene oxide polymer carrier of the bone graft material.

In some embodiments, the bioactive glass can be mixed with the alkylene oxide polymer carrier such that the bioactive glass is randomly dispersed throughout the alkylene oxide polymer carrier.

For example, the bioactive glass can be mixed with the alkylene oxide polymer carrier to form a substantially homogenous mixture (e.g., a slurry or dispersion) of carrier and bioactive glass.

In some embodiments, the bioactive glass is disposed on (e.g., coated or sprinkled onto) a surface of the alkylene oxide polymer carrier (e.g., the carrier matrix in one of a flowable, dried, or sponge-like forms).

The bioactive glass can be any alkali-containing ceramic, glass, glass-ceramic, or crystalline material that facilitates bone formation after contact with a biological environment.

Suitable bioactive glasses can include 45S5, 58S, S70C30, or a combination of the foregoing bioactive glasses.

Specifically, in some embodiments, the bioactive glass is a 45S5 bioglass comprising $SiO_2$, $Na_2O$, $CaO$ and $P_2O_5$. In embodiments the 45S5 bioglass has a nominal chemical composition of 45% silicon dioxide ($SiO_2$) (±2%), 24.5% calcium oxide (CaO) (±2%), 24.5% sodium oxide ($Na_2O$) (±2%), and 6% phosphorous pentoxide ($P_2O_5$) (±1%).

The bioactive glass can include trace or minimal amounts of at least one heavy element, including, but not limited to, arsenic (As), cadmium (Cd), mercury (Hg), lead (Pb), or a combination thereof. For example, the bioactive glass can include As in an amount less than about 3 parts per million (ppm). In another example, the bioactive glass can include Cd in an amount less than about 5 ppm. In yet another example, the bioactive glass can include Hg in an amount less than about 5 ppm. In still another example, the bioactive glass can include Pb in an amount less than about 30 ppm. Specifically, in some embodiments, the bioactive glass is a 45S5 bioglass of the composition described above and including 3 ppm As, 5 ppm Cd, 5 ppm Hg, and 30 ppm Pb.

The bioactive glass can be in any suitable form. For example, in some embodiments, the bioactive glass is in particulate form. In the particulate form, the bioactive glass particles are discrete and generally not interconnected. As such, the bioactive glass particles, collectively, are generally amorphous. In other words, the bioactive glass particles, collectively, generally lack an intentional structure or organization. The bioactive glass particles can be generally irregular in shape. The bioactive glass particles can have a smooth surface.

The bioactive glass particles can be any suitable size. In some embodiments, at least a portion of the bioactive glass particles are within a range of about 1 μm to about 1000 μm, or about 1 μm to about 900 μm, or about 1 μm to about 800

μm, or about 1 μm to about 700 μm, or about 1 μm to about 600 μm, or about 1 μm to about 500 μm, or about 1 μm to about 400 μm, or about 1 μm to about 300 μm, or about 1 μm to about 200 μm, or about 1 μm to about 100 μm in size.

In other embodiments, at least a portion of the bioactive glass particles are within a range of about 100 μm to about 1000 μm, or about 100 μm to about 900 μm, or about 100 μm to about 800 μm, or about 100 μm to about 700 μm, or about 100 μm to about 600 μm, or about 100 μm to about 500 μm, or about 100 μm to about 400 μm, or about 100 μm to about 300 μm, or about 100 μm to about 200 μm in size.

In other embodiments, at least a portion of the bioactive glass particles are within a range of about 200 μm to about 1000 μm, or about 200 μm to about 900 μm, or about 200 μm to about 800 μm, or about 200 μm to about 700 μm, or about 200 μm to about 600 μm, or about 200 μm to about 500 μm, or about 200 μm to about 400 μm, or about 200 μm to about 300 μm in size.

In other embodiments, at least a portion of the bioactive glass particles are within a range of about 300 μm to about 1000 μm, or about 300 μm to about 900 μm, or about 300 μm to about 800 μm, or about 300 μm to about 700 μm, or about 300 μm to about 600 μm, or about 300 μm to about 500 μm, or about 300 μm to about 400 μm in size.

In other embodiments, at least a portion of the bioactive glass particles are within a range of about 200 μm to about 430 μm, or about 200 μm to about 425 μm, or about 200 μm to about 420 μm in size, or about 210 μm to about 430 μm, or about 210 μm to about 425 μm, or about 210 μm to about 420 μm in size.

In other embodiments, at least a portion of the bioactive glass particles are within a range of about 212 μm to about 420 μm, or about 212 μm to about 425 μm in size.

In other embodiments, the bioactive glass particles have an average particle size of about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, or about 430 μm, inclusive of all ranges and subranges there between.

The bioactive glass can include particles of various sizes; for example, of various sizes within at least one of the foregoing ranges. In some embodiments, the bioactive glass particles are sufficiently large to prevent the particles from leaching out of the alkylene oxide polymer carrier.

In some embodiments, at least 55% of the bioactive glass particles are within a range of about 212 μm to about 425 μm in size. In some embodiments, at least 65% of the bioactive glass particles are within a range of about 212 μm to about 425 μm in size. In some embodiments, at least 75% of the bioactive glass particles are within a range of about 212 μm to about 425 μm in size. In some embodiments, at least 85% of the bioactive glass particles are within a range of about 212 μm to about 425 μm in size. In some embodiments, at least 90% of the bioactive glass particles are within a range of about 212 μm to about 425 μm in size. In some embodiments, at least 95% of the bioactive glass particles are within a range of about 212 μm to about 425 μm in size. In some embodiments, 100% of the bioactive glass particles are within a range of about 212 μm to about 425 μm in size.

In some embodiments, about <2% of the bioactive glass particles have a particle size>425 μm, about 92% of the bioactive glass particles have a particle size from 212-425 μm, and about <7% of the bioactive glass particles have a particle size<212 μm.

Any suitable method of measuring the bioactive glass particle size may be used. For example, the bioactive glass particles can be sieved using ASTM sieves according to ASTM E 11-70 (1995) method. When using such a method, for example, particles (or granules) retained between 40 and 70 mesh can be used in the moldable bone graft composition. Because particles screened within a certain range may contain a small amount of smaller particles due to screen blinding, a precision screen may be used to determine the amount of particles within the desired particle size range.

Calcium Phosphate Particles

The calcium phosphate of the moldable bone graft composition also facilitates the regrowth of bone at the target repair site.

In some embodiments, the calcium phosphate of the moldable bone graft composition is an osteoconductive agent. The calcium phosphate is disposed on, embedded within, suspended within, and/or otherwise mixed with the alkylene oxide polymer carrier.

In some embodiments, the calcium phosphate can be mixed with the alkylene oxide polymer carrier such that the calcium phosphate is randomly dispersed throughout the carrier.

For example, the calcium phosphate can be mixed with the alkylene oxide polymer carrier to form a substantially homogenous mixture (e.g., a slurry or dispersion) of carrier and calcium phosphate. In another example, the calcium phosphate can be mixed with the alkylene oxide polymer carrier and the bioactive glass.

The calcium phosphate can include any suitable calcium phosphate or mineral thereof, including, but not limited to, hydroxyapatite (sometimes referred to as hydroxylapatite; also referred to herein as "HA"), tricalcium phosphate (also referred to herein as "TCP"), β-tricalcium phosphate (also referred to herein as β-TCP, or beta-TCP) or a combination of the foregoing.

In some embodiments, the calcium phosphate is biphasic and includes tricalcium phosphate and hydroxyapatite. For example, the calcium phosphate can be biphasic and include HA and β-TCP. In one aspect, the moldable bone graft compositions taught herein comprise biphasic HA/β-TCP particles that contain about 20-60% hydroxyapatite and about 40-80% β-tricalcium phosphate. In some aspects, the moldable bone graft compositions taught herein comprise biphasic HA/β-TCP particles that contain about 60% hydroxyapatite and about 40% β-tricalcium phosphate.

The calcium phosphate can be in any suitable form. For example, the calcium phosphate can be in particulate or granular form. The calcium phosphate can be of any suitable size. For example, in some embodiments, the calcium phosphate includes mineral particles within the range of about 1 mm to about 2 mm in size. In some embodiments, the calcium phosphate includes mineral particles within the range of about 1 mm to about 2.5 mm. In some embodiments, the calcium phosphate includes mineral particles within the range of about 0.5 mm to about 2 mm in size. In some embodiments, the calcium phosphate includes mineral particles within the range of about 0.5 mm to about 2.5 mm.

In some embodiments, at least a portion of the calcium phosphate particles are within a range of about 500 μm to about 3000 μm, or about 500 μm to about 2500 μm, or about 500 μm to about 2000 μm in size.

In some embodiments, at least a portion of the calcium phosphate particles are within a range of about 1000 μm to about 3000 μm, or about 1000 μm to about 2500 μm, or about 1000 μm to about 2000 μm in size.

In some embodiments, about 10-99% of the calcium phosphate particles have a granule size of about 1000-2000 µm. In some embodiments, about 20-99% of the calcium phosphate particles have a particle size of about 1000-2000 µm. In some embodiments, about 30-99% of the calcium phosphate particles have a particle size of about 1000-2000 µm. In some embodiments, about 40-99% of the calcium phosphate particles have a particle size of about 1000-2000 µm. In some embodiments, about 50-99% of the calcium phosphate particles have a particle size of about 1000-2000 µm. In some embodiments, about 60-99% of the calcium phosphate particles have a particle size of about 1000-2000 µm. In some embodiments, about 70-99% of the calcium phosphate particles have a particle size of about 1000-2000 µm. In some embodiments, about 80-99% of the calcium phosphate particles have a particle size of about 1000-2000 µm. In some embodiments about 90%, or more, of the calcium phosphate particles have a particle size of about 1000-2000 µm.

In some embodiments, about 10-70% of the calcium phosphate particles have a particle size of about 425-1000 µm. In some embodiments, about 10-50% of the calcium phosphate particles have a particle size of about 710-1000 µm. In some embodiments, about 1-30% of the calcium phosphate particles have a particle size of about 425-710 µm.

In some embodiments, about <1% of the calcium phosphate particles have a particle size>2000 µm, about 63% of the calcium phosphate particles have a particle size from 1000-2000 µm, about 27% of the calcium phosphate particles have a particle size from 710-1000 µm, and about 9% of the calcium phosphate particles have a particle size of 425-710 µm.

oxide polymer carrier, about 25% to about 35% by weight of biphasic calcium phosphate particles, and about 5% to about 10% by weight of a bioactive glass.

In some embodiments, a moldable bone graft composition includes 60%±30% by weight of an alkylene oxide polymer carrier, 32%±30% by weight of biphasic calcium phosphate particles, and 8%+30/−7% by weight of a bioactive glass.

In some embodiments, a moldable bone graft composition includes 60%+20% by weight of an alkylene oxide polymer carrier, 32%±20% by weight of biphasic calcium phosphate particles, and 8%+20/−7% by weight of a bioactive glass.

In some embodiments, a moldable bone graft composition includes 60%±10% by weight of an alkylene oxide polymer carrier, 32%±10% by weight of biphasic calcium phosphate particles, and 8%+10/−7% by weight of a bioactive glass.

In some embodiments, a moldable bone graft composition includes 60%±5% by weight of an alkylene oxide polymer carrier, 32%±5% by weight of biphasic calcium phosphate particles, and 8%±5% by weight of a bioactive glass.

In some embodiments, a moldable bone graft composition includes 60%±1% by weight of an alkylene oxide polymer carrier, 32%±1% by weight of biphasic calcium phosphate particles, and 8%±1% by weight of a bioactive glass.

In some embodiments, a moldable bone graft composition includes about 60% by weight of an alkylene oxide polymer carrier, about 32% by weight of biphasic calcium phosphate particles, and about 8% by weight of a bioactive glass.

In one embodiment, the moldable bone graft composition comprises about 60% by weight of an alkylene oxide polymer carrier, about 32% by weight of biphasic calcium phosphate particles, and about 8% by weight of a bioactive glass, and each of the components is composed of the elements as set forth below in Table 1 at the indicated percentages wt./wt.

TABLE 1

| | PEG 1450 | PEG 400 | >2000 microns | 1000-2000 microns | 710-1000 microns | 425-710 microns | >425 microns | 212-425 microns | <212 microns |
|---|---|---|---|---|---|---|---|---|---|
| Polymer Carrier (60%) | 48% | 12% | | | | | | | |
| Biphasic Calcium Phosphate (32%) | | | <1% | 63% | 27% | 9% | | | |
| Bioactive Glass (8%) | | | | | | | <2% | 92% | <7% |

Weight Ratios of Bone Graft Compositions

Moldable bone graft compositions of various weight ratios of alkylene oxide polymer, bioactive glass, and calcium phosphate are contemplated.

In some embodiments, a moldable bone graft composition includes about 40% to about 80% by weight of an alkylene oxide polymer carrier, about 10% to about 50% by weight of biphasic calcium phosphate particles, and about 1% to about 40% by weight of a bioactive glass, wherein the calcium phosphate and bioactive glass together comprise about 20% to about 60% by weight of the bone graft composition.

In some embodiments, a moldable bone graft composition includes about 50% to about 70% by weight of an alkylene oxide polymer carrier, about 25% to about 40% by weight of a biphasic calcium phosphate particles, and about 1% to about 15% by weight of a bioactive glass, wherein the calcium phosphate and bioactive glass together comprise about 30% to about 50% by weight of the bone graft composition.

In some embodiments, a moldable bone graft composition includes about 55% to about 65% by weight of an alkylene In other embodiments, the moldable bone graft components set forth above in Table 1 have a range of ±30% of each component, or a range of ±20% of each component, or a range of ±10% of each component, or a range of ±5% of each component, or a range of ±1% of each component.

In the foregoing examples, the alkylene oxide polymer, bioactive glass, and calcium phosphate can be any alkylene oxide polymer, bioactive glass, and calcium phosphate, respectively, described herein. For example, the calcium phosphate can be biphasic and include about 60% HA and about 40% β-TCP.

In embodiments, the moldable bone graft composition is, prior to implantation into the patient's body, free of additional components including, but not limited to, bone or forms thereof (e.g., bone particles, bone powder, demineralized bone matrix), cells, tissue particles, blood products, calcium phosphate, rubber, gelatin, bone morphogenetic proteins, growth factors, anti-inflammatory agents, drugs, and radiopaque particles.

Target Repair Site Applications

As noted above, a moldable bone graft composition according to an embodiment can be used at various target repair sites within a body of a patient to facilitate bone growth therein.

In some embodiments, the moldable bone graft composition is used at a target repair site in the patient's spine. For example, as shown in FIG. 1A, a moldable bone graft composition 10 can be disposed in an opening between a transverse process of a first vertebra and a transverse process of a second vertebra. In this manner, the moldable bone graft composition can facilitate growth of a bony bridge between the transverse processes of the first and second vertebrae, such as to achieve posterolateral spinal fusion.

Figure 1B:
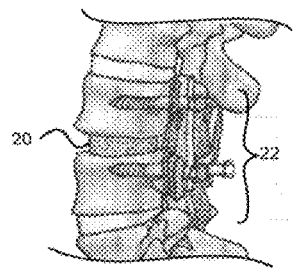
FIG. 1B is a side view of bone graft compositions according to embodiments disposed between vertebral bodies and on posterior portions of vertebrae.

In another example, as shown in FIG. 1B, a moldable bone graft composition 20 can be disposed in a void or opening between a body of a first vertebra and a body of a second vertebra different than the first vertebra. In this manner, for example, the moldable bone graft composition can facilitate growth of bone between the body of the first vertebra and the body of the second vertebra to achieve interbody fusion of the vertebrae. Referring again to FIG. 1B, in some embodiments, a plurality of moldable bone graft composition implants 22 can be positioned adjacent a posterior portion of the spine, for example, to facilitate growth of a bony bridge between adjacent vertebrae. In this manner, the plurality of moldable bone graft composition implants 22 can facilitate fusion of the adjacent vertebrae. In some embodiments, such as in a spinal fusion procedures, the moldable bone graft composition is used in conjunction with a mechanical support (e.g., a plurality of screws and/or rods, as shown in FIG. 1B).

Figure 1C:
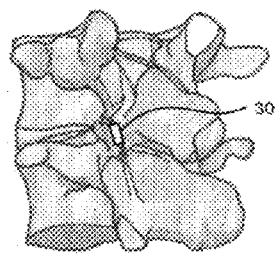
FIG. 1C is a side view of a bone graft composition according to an embodiment disposed proximate to a facet joint of a spine.

In still another example, referring to FIG. 1C, a moldable bone graft composition 30 can be implantable in, or proximate to, a facet joint of adjacent vertebrae to facilitate growth of bone at the facet joint.

Figure 1D:
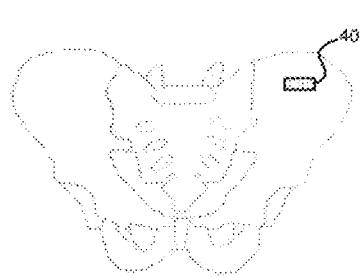
FIG. 1D is an anterior view of a bone graft composition according to an embodiment disposed on an ilium.

In some embodiments, a moldable bone graft composition is used at a target repair site in the patient's pelvis. For example, as shown in FIG. 1D, a moldable bone graft composition 40 can be disposed in an opening in the patient's ilium.

Figure 1E:
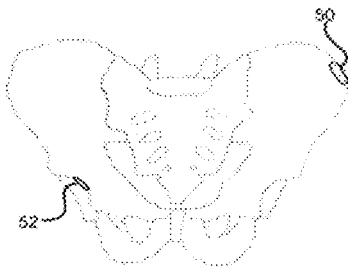
FIG. 1E is an anterior view of bone graft compositions according to embodiments disposed at an iliac crest and an acetabulum.

In some embodiments, a moldable bone graft composition is disposed in, or at a target repair site, at a different portion of the pelvis, such as, for example, the iliac crest (e.g., moldable bone graft composition 50 shown in FIG. 1E), acetabulum (e.g., moldable bone graft composition 52 shown in FIG. 1E), ischium, or pubis.

Figure 1F:
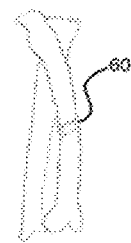
FIG. 1F is a side view of a bone graft composition according to an embodiment disposed in a radius (which is shown adjacent an ulna).
Figure 1G:
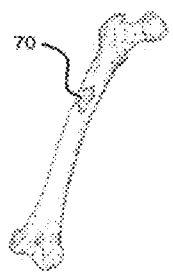
FIG. 1G is a perspective view of a bone graft composition according to an embodiment disposed in a femur.

In some embodiments, a moldable bone graft composition is used at a target repair site in a bone of an extremity of the patient. For example, a moldable bone graft composition can be disposed in an opening in the radius (e.g., moldable bone graft composition 60 in FIG. 1F), ulna, humerus, tibia, fibula, femur (e.g., moldable bone graft composition 70 in FIG. 1G), or other bone of an extremity.

Figure 1H:
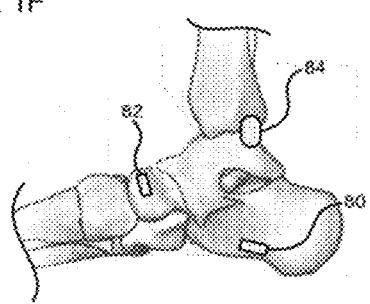
FIG. 1H is a side view of bone graft compositions according to embodiments disposed on bones of a foot and at an ankle joint.

In another example, the moldable bone graft composition can be configured to be disposed in an opening in a knee joint. In yet another example, referring to FIG. 1H, a moldable bone graft composition is disposed in an opening in a bone of the patient's foot. For example, in some embodiments, the moldable bone graft composition is disposed in an opening of a calcaneus (i.e., heel bone) (e.g., moldable bone graft composition 80), navicular (e.g., moldable bone graft composition 82), talus, cuboid, or cuneiform bone of the foot. In another example, referring to FIG. 1H, a moldable bone graft composition can be in the form of an implant 84 disposed at a target repair site in, or proximate to, an ankle joint, i.e., between the tibia and the talus.

Figure 2A:
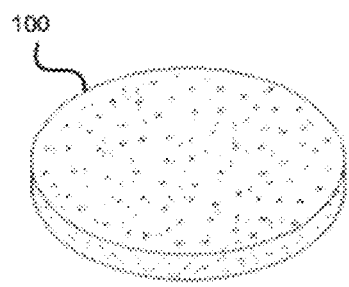
FIG. 2A is a perspective view of a bone graft material according to an embodiment.
Figure 2B:
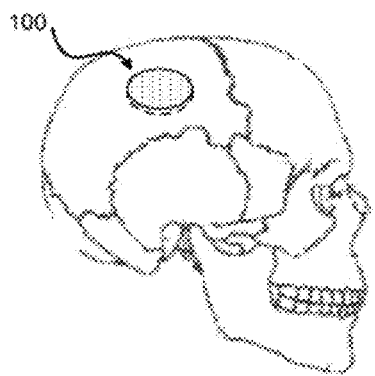
FIG. 2B is the bone graft material of FIG. 2A implanted into a bone void in a cranium.

In some embodiments, referring to FIGS. 2A-2B, the moldable bone graft composition can be in the form of an implant 100 in or at a target repair site in a patient's cranium to facilitate growth of bone therein. Although specific examples of suitable target repair sites have been illustrated and described, in other embodiments, the moldable bone graft composition can be configured to be implanted into or at a target repair site in a different bone or bony structure of the patient's body.

Moldable Bone Graft Composition Kits

A moldable bone graft material kit, according to an embodiment, includes at least a bioresorbable polymer carrier, such as an alkylene oxide polymer, and bioactive glass (e.g., in the form of particles), and calcium phosphate particles.

In one embodiment, the moldable bone graft composition is supplied as an implant preloaded into a syringe. The implant comprises the bioresorbable polymer carrier and bioactive glass.

In one embodiment, the moldable bone graft composition kits comprise a bone graft syringe assembly for delivering the bone graft material. The bone graft syringe assembly comprises: 1) a syringe barrel having a proximal end, a distal end, and an inner chamber adapted for receiving the moldable bone graft composition, the inner chamber having a proximal opening and a distal opening, and 2) a plunger adapted for expelling the moldable bone graft material through the distal opening of the inner chamber, with the plunger slidably received within the inner chamber through the proximal opening.

Methods of Making the Present Moldable Bone Graft Compositions

A method of making a bone graft material according to an embodiment is described herein. The implant is sold already mixed supplied in a syringe.

In one embodiment, the polymer carrier is melted and the bioglass and mineral components are added. The composite is cooled, and the bulk material is hand molded into individual implants.

In certain aspects, these individual implants are loaded into a syringe and sold to a consumer as a preloaded syringe.

Methods of Using the Present Moldable Bone Graft Compositions

A bone graft procedure, according to an embodiment, includes a method for implanting a moldable bone graft material or composition (including any moldable bone graft material or composition described herein) at a target repair site within a body of a patient.

The bone graft procedure optionally includes preparing the target repair site of the bone or bony structure within the patient's body to receive the bone graft material. Preparation of the target repair site can include cleansing the site to remove foreign materials, loose bone fragments or powder, or other potentially harmful materials. In some procedures, preparation of the target repair site includes re-shaping the site, for example, by removing a portion of the perimeter of the site so that the site has a desired shape. In other procedures, preparation of the target repair site includes decortication to the level of bleeding bone.

The bone graft procedure optionally includes shaping the moldable bone graft material for placement at the target repair site. For example, the physician can manually manipulate (e.g., squeeze, pinch, stretch, etc.) the moldable bone graft material. In some embodiments, shaping the bone graft material includes forming the bone graft material into a desired shape.

The bone graft procedure includes positioning the bone graft material at the target repair site. In some embodiments, positioning the bone graft material includes injecting the bone graft material in a flowable state into the target repair site. For example, the bone graft material can be in the form of a slurry, foam, paste, solution, or the like, which is injected into the target repair site via a syringe, or elongated tube, such as in minimally invasive surgery (MIS).

Optionally, at the physician's discretion, the bone graft procedure includes wetting the bone graft material with a suitable solution before or after positioning the bone graft material at the target repair site. In some embodiments, the bone graft material is wetted with a fluid from the patient's body. For example, blood or plasma from the patient's body can be disposed on or permitted to flow to the bone graft material.

At the physician's discretion, the bone graft procedure includes mixing the bone graft material with autologous bone, allograft, or a mixture of the two.

In one embodiment, the moldable bone graft composition is supplied in a homogeneous and "ready to use" fashion. In aspects, this "ready to use" fashion is embodied as a moldable bone graft composition preloaded into a syringe. In this embodiment, the surgeon only has to eject the composition from the syringe, knead it with manual force (because in an aspect the composition starts as a cylindrical plug loaded into the syringe), then mold the composition to the desired shape, and apply the composition to the target repair site.

The bone graft procedure optionally includes closing an aperture in the patient's body that provided access to the target repair site. For example, a skin flap can be repositioned over the implanted bone graft material. In some embodiments, sutures, staples, or another closure mechanism are used to help close the aperture in the patient's body. The patient can be monitored for symptoms of complication (e.g., infection, rejection of the bone graft material), as well as for regrowth of bone at the target repair site.

Specific examples of moldable bone graft compositions are now described.

EXAMPLES

Example 1

Moldable Bone Graft Composition

A synthetic bone graft composition, comprising: (1) resorbable alkylene oxide polymer (AOP) carrier, (2) biphasic granulate (HA/β-TCP, 60:40), and (3) 45S5 bioactive glass, in a single homogenous and moldable implant, was prepared.

The moldable bone graft composition comprised the components as previously set forth in Table 1.

The moldable bone graft composition was found to provide optimal intra-operative handling, sustained bioactivity, and a resorption profile that allows gradual and consistent defect remodeling consistent with the host remodeling response.

The utilized particle size range of the bioactive glass component (212-425 μm) has demonstrated advantages over the more common broader ranges featured in commercial bioactive glass products.

It was discovered that a narrow particle size distribution will yield a more controlled rate of ion dissolution and surface reactivity, producing a more consistent rate of bone bonding and proliferation throughout the defect site.

Smaller particles (<210 μm) can degrade quickly, causing a transient inflammatory response that may impede the up-regulation of osteoprogenitor cells. Larger particles (>420 μm) may not fully degrade, leaving unreacted glass particles at the defect site that can delay osteoconduction and remodeling. In addition, 45S5 bioactive glass has been shown to be antimicrobial, bioactive, and osteostimulatory in simulated physiological environments.

The utilized biphasic mineral granulate provides distinct advantages over HA and β-TCP based materials, in terms of implant resorption and remodeling.

Hydroxyapatite (HA) is largely insoluble with bone bonding limited to the surface. Despite compositional modifications such as "silicate substitution," the potential for limited resorption and remodeling remains, which may leave the defect site susceptible to focused mechanical stress. See, e.g., Vaccaro A R. The Role of the Osteoconductive Scaffold in Synthetic Bone Graft. Orthopedics 2002, 25(5):571-78; and also Szpalski M, Gunzburg R. Applications of Phosphate-Based Cancellous Bone Void Fillers in Trauma Surgery. Orthopedics 2002, 25(5):601-09.

Beta tricalcium phosphate (β-TCP) is similar in composition to amorphous bone precursors and readily undergoes remodeling, stimulated by the material's calcium phosphate-rich surface layers. However, β-TCP can potentially resorb faster than the rate of new bone formation, resulting in non-mineralized fibrous tissue at the implant site. Despite enhancements to β-TCP, as with Vitoss Scaffold Foam Pack (Orthovita), resorption of β-TCP has been reported to be unpredictable in biological environments. See, e.g., Vaccaro A R. The Role of the Osteoconductive Scaffold in Synthetic Bone Graft. Orthopedics 2002, 25(5):571-78; Szpalski M, Gunzburg R. Applications of Phosphate-Based Cancellous Bone Void Fillers in Trauma Surgery. Orthopedics 2002, 25(5):601-09; Hing K A, Wilson L F, Revell P A, Buckland T. Comparative performance of three bone graft substitutes. Spine J 2007, 7(4):475-90; and also Betz R R. Limitations of Autograft and Allograft: New Synthetic Solutions. Orthopedics 2002, 25(5):561-70.

To address the limitations of these biomaterials, the presently utilized biphasic calcium phosphate materials combine the long term stability of HA with the solubility of β-TCP, which results in an osteoconductive material with a gradual and controlled resorption profile optimal for bone defect remodeling.

Thus, the present biphasic HA/β-TCP calcium phosphate particles, in a 60:40 ratio of HA to β-TCP, were unexpectedly superior to HA or β-TCP particles utilized in isolation. The combination of these particles, in the specified ratio and at the specified particle size, yields superior results.

Example 2

Demonstration of Bioactivity of Bioactive Glass Component

Figure 3:
FIG. 3 is an SEM image that illustrates the in vitro testing of a moldable bone graft composition in simulated body fluid at time point zero and at 1 day and at 7 days. The moldable bone graft composition demonstrated apatite layer formation on the bioactive glass surface in as early as 1 day.

The bioactive glass component of the moldable bone graft composition utilized in Example 1 undergoes a unique surface modification within the physiological environment that allows for direct bonding with surrounding bone. Following implantation, an exchange of biologically active ions produces a bioactive hydroxy carbonate apatite (HCA) layer to which bone can readily bond to. These surface reactions are followed by the proliferation and differentiation of bone related cells on the apatite matrix as part of the normal healing process. For example, the moldable bone graft composition taught herein demonstrated apatite layer formation in a simulated body fluid (SBF) on the bioactive glass surface in as early as 1 day (FIG. 3).

We have determined that particle size distribution of bioactive glass is a critical factor to bone bonding performance. The particle size range of the bioactive glass (212-425 µm) utilized in the present experiment has demonstrated advantages over the more commonly utilized 90-710 µm range (Novabone), including higher rates of new bone formation and material remodeling at the defect site. See, Yang S S. Compositions and Methods to Repair Osseous Defects. U.S. Pat. No. 6,228,386 (2001), incorporated by reference herein. Generally, a narrow particle size distribution will yield a more controlled rate of ion dissolution and surface reactivity, producing a more consistent rate of bone bonding and proliferation throughout the defect site. Smaller particles (<210 µm) can degrade quickly, causing a transient inflammatory response that may impede the up-regulation of osteoprogenitor cells. Larger particles (>420 µm) may not fully degrade, leaving unreacted glass particles at the defect site that can delay osteoconduction and remodeling. See, Schepers E J G, Oucheyne P., Bioactive glass particles of narrow size range for the treatment of oral bone defects: a 1-24 month experiment with several materials and particle sizes and size ranges. J Oral Rehab 1997, 24:171-181.

Example 3

Demonstration of Biphasic Remodeling

Hydroxyapatite (HA) is similar in composition to human bone. However, the material is largely insoluble, with bone bonding limited to the surface. Despite compositional modifications such as "silicate substitution" as with Actifuse ABX (Apatech/Baxter), the potential for limited resorption and remodeling remains, which may leave the defect site susceptible to focused mechanical stress. See, e.g., Vaccaro A R. The Role of the Osteoconductive Scaffold in Synthetic Bone Graft. Orthopedics 2002, 25(5):571-78; Szpalski M, Gunzburg R. Applications of Phosphate-Based Cancellous Bone Void fillers in Trauma Surgery. Orthopedics 2002, 25(5):601-09.

Beta tricalcium phosphate (β-TCP) is similar in composition to amorphous bone precursors and readily undergoes remodeling, stimulated by the material's calcium phosphate rich surface layers. See, e.g., Szpalski M, Gurizburg R. Applications of Phosphate-Based Cancellous Bone Void fillers in Trauma Surgery. Orthopedics 2002, 25(5):601-09; Hing K A. Wilson Lf, Revell P A, Buckland T. Comparative performance of three bone graft substitutes. Spine J 2007, 7(4):475-90. However, β-TCP can potentially resorb faster than the rate of new bone formation, resulting in non-mineralized fibrous tissue at the implant site. Id. Despite enhancements to β-TCP, as with Vitoss Scaffold Foam Pack (Orthovita), resorption of β-TCP has been reported to be unpredictable in biological environments. Id., and see also, Betz R R. Limitations of Autograft and Allograft: New Synthetic Solutions. Orthopedics 2002, 25(5):561-70.

To address the limitations of these biomaterials, the present biphasic calcium phosphate materials, utilized in the moldable bone graft compositions, combine the long term stability of HA with the solubility of β-TCP, resulting in an osteoconductive material with a gradual and controlled resorption profile optimal for bone defect remodeling.

Specifically, biphasic mineral formulated in a 60:40 (HA: β-TCP) ratio, as featured with the present moldable bone graft compositions, has demonstrated advantageous bone remodeling properties in both bench testing and in clinically relevant animal studies. See, Daculsi G, Laboux O, Malard O, Weiss P. Current state of the art of biphasic calcium phosphate bioceramics J Mater Sci. Mater Med 2003, 14:195-200; Fellah B H, Gauthier O, Weiss P, Chappard D, Layrolle P. Osteogenicity of biphasic calcium phosphate ceramics & bone autograft in a goat model. Biomaterials 2008, 29:1177-1188; Legeros R Z, Lin S, Rohanizadeh R, Mijares D, Legeros J P. Biphasic calcium phosphate bioceramics: preparation, properties & applications. J Mater Sci Mater Med 2003, 14:201-09. Following implantation, dissolution of biphasic mineral produces a direct bonding interface with host bone through the release of calcium and phosphate ions and subsequent formation of a surface apatite layer similar to bone mineral. Id.

In addition, the structural microporosity and macroporosity of the presently utilized biphasic granules (1-2 mm) are in the optimal ranges needed to allow penetration of biological fluids (>10 µm) and to support osteoconductivity (>100 µm), providing a more sustained remodeling response at the defect site. Clinical studies have shown efficacy of macroporous and macroporous biphasic calcium phosphate in the reconstruction of large bony defects, including in posterior spinal fusion procedures, and suggest biphasic mineral is a safe alternative to autografts and allografts. See, Garrido C A, Lobo S E, Turibio F M, Legeros R Z. Biphasic calcium phosphate bioceramics for orthopaedic reconstructions: clinical outcomes. Intl Biomoter 2011, 2011:129727; Xie Y, Chopin D, Morin C, Hardouin P, Zhu Z, Tang J, Lu J. Evaluation of the osteogenesis and biodegradation of porous biphasic ceramic in the human spine. Biomoteriols 2006, 27(13):2761-7; Betz R R. Limitations of Autograft and Allograft: New Synthetic Solutions. Orthopedics 2002, 25(5):561-70.

Figure 4:
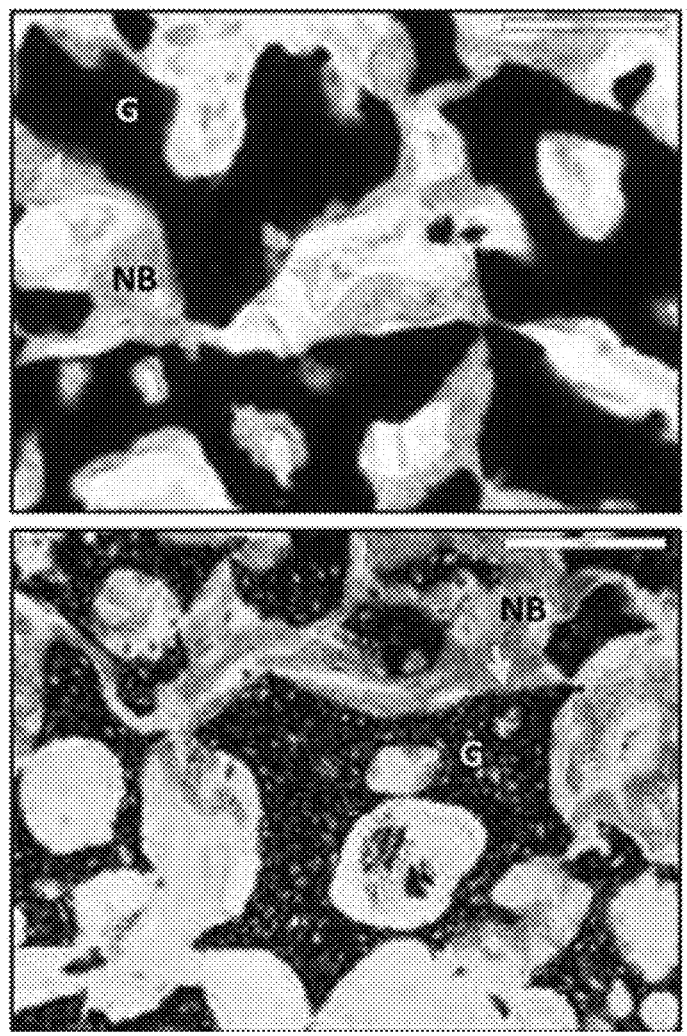
FIG. 4 is a histology stain that illustrates surface resorption of the biphasic mineral utilized in the moldable bone graft compositions taught herein (top panel) is superior to that of HA-based Actifffise ABX granules (bottom panel). G=granules, NB=new bone.

Thus, the biphasic mineral granulate utilized in the present disclosure provides distinct advantages over HA-based materials such as Actifuse ABX in terms of implant resorption and remodeling. FIG. 4 visually demonstrates the gradual resorption of the present biphasic mineral compared to Actifuse ABX in a rabbit posterolateral spine fusion (PLF) study. See, Soden S D, Schimandle J H, Hutton H C. An Experimental Intertransverse Process Spinal Fusion Model: Radiographic, Histologic & Biomechanical Healing Characteristics. Spine. 1995, 20:412-20.

The gradual resorption rate, porosity, and microstructure of the biphasic mineral utilized in the present moldable bone graft compositions result in a stable scaffold that allows sustained osteoconductivity during the healing process.

Example 4

Demonstration of Synergistic Fusion Effect

The presently utilized combination of 45S5 bioactive glass and 60:40 biphasic mineral (HA:β-TCP) provide a synergistic composite bone graft optimized for sustained bioactivity and remodeling in posterolateral spine fusion procedures.

Figure 5:
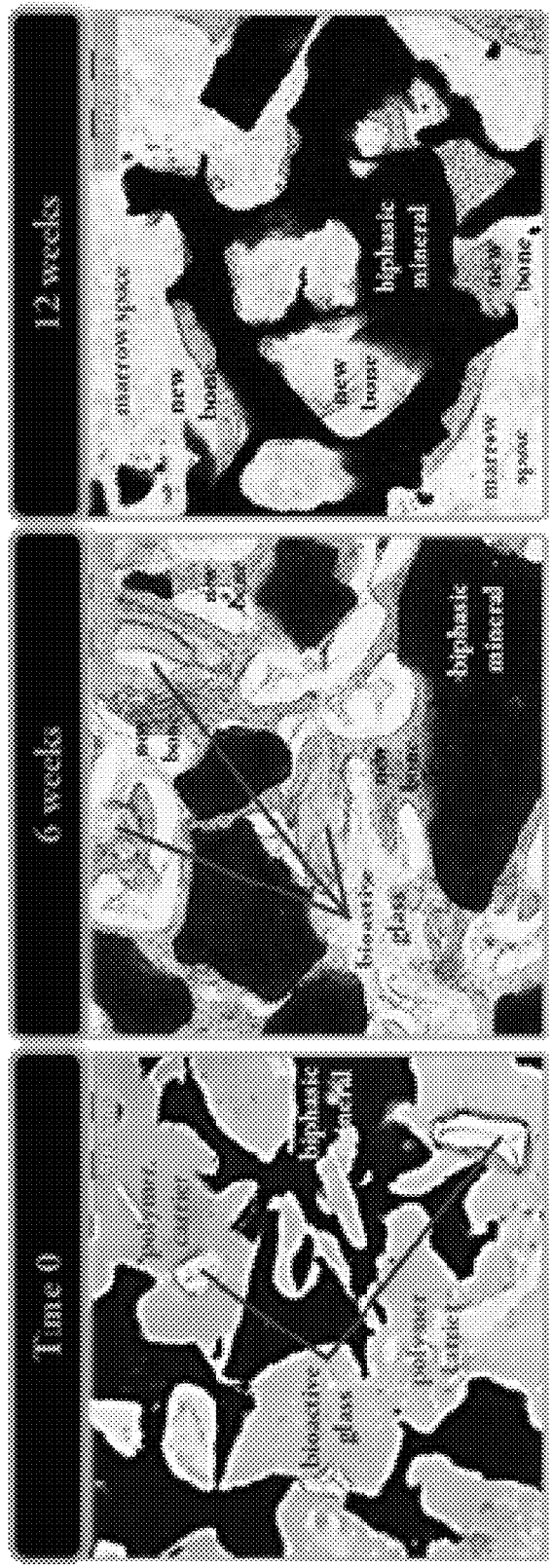
FIG. 5 is a histology slide of the bone graft composition from a rabbit posterolateral spine fusion study, demonstrating new bone formation from a starting time point 0, to 6 weeks, to 12 weeks.
Figure 6:
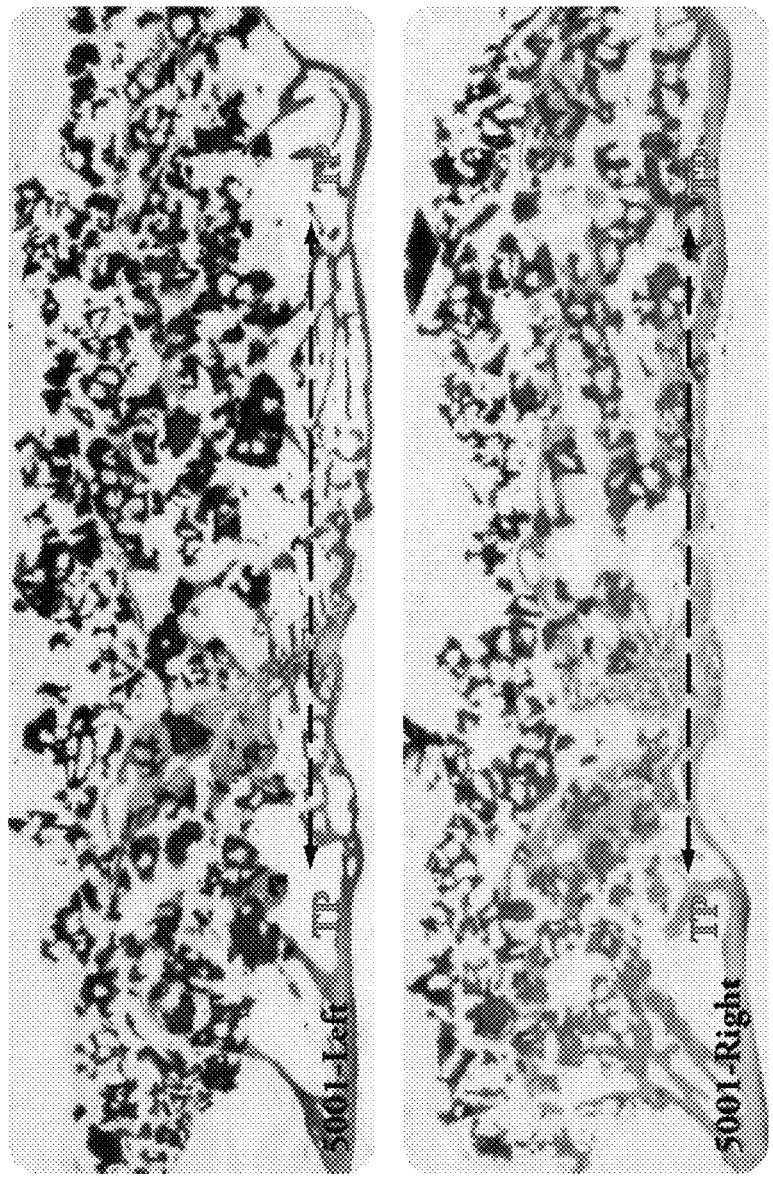
FIG. 6 is a pair of histology slides of the bone graft composition from a rabbit posterolateral spine fusion study demonstrating bilateral fusion within the same animal characterized by new mature bone formation spanning the transverse processes at 12 weeks.

FIG. 5 demonstrates the healing mechanism of action as follows: After implantation, the polymer carrier rapidly resorbs into surrounding tissues and the bioactive glass particles elicit a versatile biostimulative response throughout the matrix of biphasic granules. This response encourages the adhesion, proliferation and differentiation of bone healing cells onto the newly formed surface apatite layer, and facilitates a uniform progression of these processes to the biphasic granule matrix. The biphasic matrix resorbs in tandem with the host remodeling process to facilitate maturation of the fusion site throughout the healing process.

Thus, the representative performance of the presently taught moldable bone graft compositions in a rabbit PLF model is depicted, where bridging bone was consistently observed spanning transverse processes by 12 weeks in vivo, with new bone in direct apposition to, and dispersed between, the biphasic granules. See, Example 7, setting forth full study. See also, Boden S D, Schimandle J H, Hutton H C. An Experimental Intertransverse Process Spinal Fusion Model: Radiographic, Histologic & Biomechanical Healing Characteristics. Spine. 1995, 20:412-20.

Example 5

In Vitro Bioactivity Test

The in vitro bioactivity of the present moldable bone graft compositions was evaluated using the currently accepted definition and endpoint of hydroxyapatite (HA) formation and deposition on the surfaces of glass and ceramic materials when immersed in simulated body fluid (SBF), according to International Standard ISO 23317, Implants for Surgery—In vitro evaluation for apatite-forming ability of implant materials.

Test samples included the moldable bone graft composition of the present disclosure comprising 45S5 bioactive glass and biphasic mineral HA/β-TCP granules, biphasic granules extracted from the finished device, 45S5 bioactive glass raw particles used in the fabrication of the finished device, and a commercially available moldable bone graft material comprising silicate-substituted hydroxyapatite (HA) granules (1-2 mm) suspended in a resorbable polymer carrier.

A non-apatite forming glass, composition in mol %: 70 $SiO_2$, 15 $Na_2O$, 15 CaO, formed into 10 mm diameter disks was used as a control as derived from Annex B from ISO/FDIS 23317:2007 (E).

The moldable bone graft composition of the present disclosure, as well as the comparative material, were thoroughly mixed by hand, shaped into a 2.5 cc (3.75 gram) ball, and placed into SBF. Samples each weighing 0.3-0.5 grams were immersed in 100 ml of simulated body fluid (SBF) at 37° C. for 1, 7, 14, and 28 days and evaluated by X-ray diffraction (XRD), and for pH and weight changes at each time point. SEM images were taken of all sample sets for comparison.

The polymer carrier dissolved in the SBF similar to how it would in the body. All experiments were run in triplicate.

X-ray diffraction (XRD) was performed on 45S5 bioactive glass raw particles and the non-apatite forming glass disks using a Panalytical X'Pert Multi-Purpose Diffractometer scanning between 10 and 80° 2θ at a rate of 1°/minute XRD was not performed on the biphasic granules extracted from the finished device, the finished moldable bone graft composition of the present disclosure, or the comparative silicate-substituted HA material, because all these materials contain a significant fraction of HA as the base material, which would make identifying a new HA surface formed by the SBF solution indistinguishable from the parent materials.

No crystalline peaks were identified for the non-apatite forming glass control, before or after immersion in SBF, verifying that HA did not spontaneously precipitate on all materials.

The XRD pattern for the 45S5 raw particles had no evidence of crystalline peaks for the unreacted glass, while the 1, 7, 14, and 28 day SBF samples did form a crystalline surface layer, and the major peaks (around ~26° &32°) in the patterns corresponded to those of a HA, $Ca_{10}(PO_4)_6(OH)_2$ (JCPSD 72-1243), indicating the presence of HA on the surface of the 45S5 raw particles.

Scanning electron microscopy (Hitachi S-4700 SEM) was performed on samples that were unreacted and samples that had been immersed in SBF for 1, 7, 14, and 28 days at 37° C. The non-apatite forming glass did not precipitate any HA on the surface, verifying that the SBF was not spontaneously precipitating HA crystals on free surfaces.

The 45S5 raw particles did have a nanocrystalline HA surface present after 1, 7, 14, and 28 days in SBF confirming the results from the XRD. There was no evidence of HA crystals on the biphasic granules or the silicate-substituted HA material when compared to the unreacted surfaces. The biphasic granules extracted from the finished device did not precipitate an identifiable HA layer even in the presence of bioactive glass particles. This is not surprising since the HA precipitation on a bioactive material is a surface reaction that does not translate to other materials or surfaces even in the vicinity of the bioactive material.

This observation confirms that the combination of 45S5 bioactive glass combined with biphasic HA/β-TCP granules in a composite material provides a biological enhancement over the biphasic granules alone, via the bioactive nature of the 45S5 bioactive glass.

Example 6

Femoral Defect Animal Study

The aforementioned moldable bone graft composition set forth in Example 1 was utilized in a femoral defect animal study.

The moldable bone graft composition of the present disclosure was evaluated following implantation into distal femoral defects of skeletally mature New Zealand white rabbits. The objective of this study was to evaluate the in vivo response of the bone graft of the present disclosure, in comparison to a commercially available bone graft material comprising silicate-substituted hydroxyapatite granules suspended in a resorbable polymer carrier, when implanted in a critical-sized cancellous bone defect.

The animal model chosen provided bilateral cancellous defects (6 mm×10 mm) in the distal femur in adult rabbits that have been reported to be critical. The test groups were comparatively evaluated for host response, new bone formation, and implant resorption within the healing defects using radiographic, microCT, and histologic analyses at time points of 1 day, 6 weeks, and 12 weeks.

A total of 11 animals were implanted with the moldable bone graft composition of the present disclosure in one femur and the comparative material in the contralateral femur. One animal was sacrificed after 1 day following surgery, four animals after 6 weeks, and six animals after 12 weeks. Following sacrifice, the implant sites were evaluated and compared for the healing response using radiographic, microCT, and histological endpoints.

Animals were acclimated for at least seven days prior to surgery. Surgery was performed following standard an aseptic technique under general anesthesia as is understood in the art. A lateral incision, approximately 1.5 centimeters long, was made and the soft-tissues overlying the lateral femoral condyle dissected. A 6.0 mm drill bit was used to drill through the cortex to a depth of 10 mm under constant saline irrigation. The bone was removed, and a syringe of saline was used to wash out any remaining bone debris. The bone graft material of the present disclosure was hand-packed into the defect to the level of the original cortex using approximately 0.3 cc of material. Fascia and skin were closed in the routine manner consistent with good surgical practice. This surgical procedure was then conducted on the contralateral limb using the comparative material. Post-operative care of the animals was performed in accordance with good husbandry practices as understood in the art.

No complications were observed in either test group over the course of the study. Gross observations of the implant sites demonstrated healthy tissue absent of adverse inflammatory reactions regardless of test group or time point. Radiographic analysis indicated no adverse reactions and a normal progression in healing over time in both groups.

MicroCT scans supported the radiographic observations, demonstrating no adverse reactions and a similar osteoconductive healing response in both groups, with a progression of new bone formation and implant resorption observed over time. The 6 week microCT scans showed host integration and new bone formation originating from the defect margins in both groups. The 12 week scans showed a progression of host integration and defect remodeling from the 6 week time point, with new bone formation throughout the implant and defect site in both groups. New bone formation was apparent in direct apposition to and bridging between implant granules.

There was a pronounced change in granular surface appearance in the biphasic granules of the present disclosure's compositions that was less apparent in the silicate-substituted hydroxyapatite comparative material, indicating the more optimal resorption and remodeling response achievable with a moldable bone graft composition according to the present disclosure.

Histopathology analysis of the defect sites indicated no adverse reactions and a similar osteoconductive healing response in both groups, characterized by a progression of new bone formation and implant resorption over time. The 1 day histology images showed the defect margins and presence of the implant materials with no adverse reactions. The 6 week histology images showed host integration and new bone formation originating from the defect margins in both groups with a progression of host integration across defect sites at 12 weeks. New bone formation was apparent in direct apposition to and bridging between individual granules in both groups.

The bioactive glass component of the bone graft of the present disclosure was largely resorbed at 6 weeks and replaced by mature host bone at 12 weeks. The biphasic granule component of the present disclosure demonstrated a loss of distinction at the new bone interface that was not observed with the silicate-substituted hydroxyapatite material. Overall, the moldable bone graft composition of the present disclosure demonstrated a consistent progression from woven to mature lamellar bone, with the development of marrow spaces throughout the defect over time that was not as prevalent in the comparative material.

These observations indicate a more optimal resorption and remodeling response in the moldable bone graft compositions of the present disclosure, as compared to the silicate-substituted hydroxyapatite material, likely due to the combination of bioactive glass and biphasic mineral granulate.

Example 7

Posterolateral Spine Fusion Animal Study

The aforementioned moldable bone graft composition set forth in Example 1 was utilized in a posterolateral spine fusion rabbit model.

The moldable bone graft compositions taught herein demonstrated greater fusion rates than autograft in these experiments.

The results indicate that the standalone implant composed of the moldable bone graft composition is a viable alternative to using autograft in PLF procedures.

The use of the disclosed moldable bone graft compositions, in place of autograft in posterolateral spine fusion procedures, can reduce: surgery time, intraoperative complications, and comorbidities associated with harvesting autograft.

The moldable bone graft composition of the present disclosure was evaluated following implantation into posterolateral spine defect of skeletally mature New Zealand white rabbits. A commercially available, moldable bone graft material comprising silicate-substituted hydroxyapatite granules suspended in a resorbable polymer carrier was also evaluated in the study for comparison.

A total of 23 animals were implanted with the bone graft of the present disclosure and an additional 23 implanted with the comparative material. One animal was sacrificed after 1 day following surgery, six animals after 6 weeks, and ten animals after 12 weeks. Following sacrifice, the implant sites were evaluated and compared for biocompatibility, osteoconductive healing response and fusion using radiographic, microCT, manual palpation, biomechanical and histological endpoints.

The surgical approach to the spine was identical in all rabbits. A dorsal midline skin incision, approximately 15 centimeters long, was made from LI to the sacrum, and then the fascia and muscle were incised over the L5-L6 transverse processes (TPs). The TPs were then decorticated with a high-speed burr. Approximately 2.5-3.0 cc per side of test article was placed in the paraspinal bed between the transverse processes. Fascia and skin were closed in the routine manner consistent with good surgical practice. This surgical procedure was then conducted on the contralateral limb using the comparative material. Post-operative care of the animals was performed in accordance with good husbandry practices as understood in the art.

No clinical complications were noted in any test group over the course of the study. Necropsy of the animals was unremarkable regardless of test group. Macroscopic analysis of the implant sites demonstrated healthy tissue with no apparent adverse effects such as inflamed, necrotic, or devascularized tissue surrounding the defect sites. The entire lumbar column was removed "en-bloc". Soft tissues were immediately removed from the surgically treated spinal unit after the spine was dissected out of the body. The grafted site was examined for infection, and soft tissue abnormalities. Spines allocated for histology analysis from the 6 and 12 week animals were placed in 10% neutral buffered formalin. Spines allocated for biomechanical testing from the 12 week animals were tested immediately.

Radiographs at 6 and 12 weeks showed a normal healing response over time in both groups with a loss of graft distinction at the host bone margins, indicating a progression in host integration and new bone formation over time. No fractures, osteolysis, or other adverse reactions were evident during radiographic examination for either group. The radiographs were also assessed for fusion by two reviewers blinded to the treatment groups. The fusion masses in each animal were determined to either have bilateral bridging bone, unilateral bridging bone, no bone on either side, or indeterminate. Fusion success was defined by the presence of bilateral bridging bone, indicating both sides of the spine were fused. At 12 weeks the radiographic fusion rates were 60% (6/10 animals) for animals implanted with a bone graft composition of the present disclosure, and 50% (5/10 animals) for the comparative material.

The MicroCT scans supported the radiographic findings, showing a normal healing response over time with no adverse reactions for both test groups. The 6 week microCT scans showed host integration and new bone formation originating from the defect margins at the TPs in both groups. The 12 week scans showed a progression of new bone formation from across the defect from the 6 week time point. New bone formation was apparent in direct apposition to and bridging between implant granules.

There was a pronounced change in granular surface appearance in the biphasic granules of the present disclosure's compositions that was less apparent in the silicate-substituted hydroxyapatite comparative material, indicating the more optimal resorption and remodeling response achievable with a moldable bone graft composition according to the present disclosure.

Bilateral, microCT morphometry analysis was performed on sagittal view scans using a rectangular region of interest (ROI) of 250 mm2 placed across the fusion site inclusive of the transverse processes and along the central axis of the fusion mass. Areas of new bone and residual implant were calculated based on validated contrast parameters. At 6 weeks, the bone graft of the present disclosure demonstrated significantly greater bone area (49 vs. 31 mm2; p<0.05) and significantly lesser implant area (27 vs. 39 mm2; p<0.05) than the comparative group. The greater bone area measured in the bone graft of the present disclosure is likely due to the bioactive response elicited by the bioactive glass component. The lesser residual implant area measured in the present disclosure's bone graft is likely due to rapid dissolution and remodeling of the bioactive glass component and the solubility of the β-TCP portion of the biphasic mineral component compared to the limited resorption capability of the HA-based comparative material.

At 12 weeks, there were no statistical differences between the groups for either new bone or residual implant areas. However, although the overall morphometric area for bone was similar between groups at 12 weeks, differences in the physical structure of the remodeling bone and overall progression of defect healing were observed between the test groups. As remodeling progresses, bone will condense and align directionally according to stress across the defect. For example, the bone graft of the present disclosure demonstrated more condensed and aligned mature bone spanning between TPs, with developed marrow spaces throughout the material and defect in most animals. Conversely, the comparative group demonstrated a progression of less condensed immature bone from the margins of the TPs with less developed marrow spaces. New bone formation was not observed spanning the TPs in most animals in the comparative group.

Stiffness of the fused motion segment was assessed by biomechanical non-destructive stiffness testing was performed following manual palpation in the 12 week animals. Testing consisted of flexion/extension, lateral bending, and torsion to a pre-determined, sub-failure load. The vertebral bodies cranial and caudal to the fused motion segment were mounted in a biaxial servo-hydraulic materials testing machine retrofitted with two spine gimbals and a passive XZ table. Custom-made rigid body markers were placed on each vertebral body and the two gimbals to track the segmental motions. Nondestructive flexibility tests were performed about each axis of rotation (i.e., flexion-extension, right-left lateral bending, and right-left axial rotation) by applying an isolated ±0.27 Nm moment about each of the primary axes. Each test initiated and concluded in the neutral position with zero load. Three loading and unloading cycles were performed with motion data collected on the third cycle. The displacement of each vertebrae was measured using an optoelectronic motion capture system, the output of which was synchronized with that of the MTS. During testing, the specimens were kept moist with saline solution spray. Stiffness was determined and compared to normal controls.

At 12 weeks all groups demonstrated significantly less range of motion in all planes compared to normal unfused controls. The biomechanical fusion rate for each group was determined from the flexion-extension data based on work by Erulker et al., who determined a total range of motion (ROM) in flexion-extension of less than 5 degrees correlates to solid fusion in autograft treated specimens in a PLF rabbit model. See, Erulker J S, Grauer J N, Patel T C, Panjabi M M. Flexibility analysis of posterolateral fusions in a New Zealand white rabbit model. Spine (Phila Pa 1976). 2001 May 15, 26(10):1125-30.

This ROM threshold also holds clinical significance, as clinical studies have utilized lateral flexion-extension radiographs where less than 5 degrees is utilized as positive threshold for fusion. See, James Kang, MD, Howard An, MD, Alan Hilibrad, MD, Tim Yoon, MD, PhD, Eoin Kavanagh, MD, Scott Boden, MD. Grafton and Local Bone Have Comparable Outcomes to Iliac Crest Bone in Instrumented Single-Level Lumbar Fusions. Spine. 2012, 37:1083-1091.

Because autograft is considered the "gold standard" treatment for posterolateral spine fusion, and due to the clinical relevance of evaluating fusion via flexion-extension ROM, specimens with a ROM of less than 5 degrees in flexion-extension were determined to be "Fused" by biomechanical analysis.

The bone graft of the present disclosure demonstrated a biomechanical fusion rate of 89% (8/9 animals), while the comparative material demonstrated a fusion rate of 44% (4/9 animals).

Of significant note, is that the 80% fusion rate demonstrated by a bone graft of the present disclosure is higher than the 63% (5/8 animals) fusion rate reported by Erulker et al. for ICBG autograft, considered the "gold standard" in the clinical setting.

Histopathology analysis of the decalcified paraffin embedded, H&E stained fusion sites indicated no adverse reactions and a normal healing response over time in both groups. The majority of the fusion sites, regardless of implant type or time of implantation, had minimal inflammation. Most often there were very low numbers of macrophages and multinucleated giant cells (which in some cases could be osteoclasts) with some scattered, often rare lymphocytes and plasma cells. In all sections there is moderate neovascularization and fibrosis. Most of the tissues had moderate new bone formation. New bone formation was not specifically scored, but at both the 6 and 12 week time points it appeared that the bone graft of the present disclosure had the most abundant new bone formation and remodeling as opposed to the comparative material. This is likely due to the rapid dissolution and remodeling of the bioactive glass component, which appeared to have been resorbed and replaced by mature host bone at 12 weeks. The biphasic HA/β-TCP granules appeared to be remodeling based on changes in granular appearance and loss of distinction at the new bone interface over time, which were not as apparent in the HA-based comparative material.

In the bone grafts of the present disclosure, at 6 weeks, there was no evidence of acute inflammation and the primary cell types present at the implant sites were that of macrophages and giant cells with fewer lymphocytes and plasma cells. These cell types were most likely present to clean up debris associated with the surgery site. The giant cells were commonly associated with the implant and/or new bone so therefore could be osteoclasts. There was moderate, to sometimes abundant, fibrous connective tissue along with neovascularization, which is not surprising and likely served as a scaffold for new bone formation.

In the bone grafts of the present disclosure, at the 12 week time point, there was a similar pattern of mild to moderate inflammatory cell infiltrates, with macrophages and giant cells predominating along with fewer numbers of scattered lymphocytes and plasma cells. The increase in macrophages and giant cells from the 6 week time point is likely due to bone and/or tissue remodeling. There were certainly more giant cells associated with new bone and/or implant material suggestive of osteoclast remodeling. In light of this, there are an increased number of macrophages to clean up associated cellular debris. Again, neovascularization and fibrosis are expected and the score is similar to that at 6 weeks.

Bilateral, histomorphometry analysis was performed on calcified plastic embedded, H&E stained sections using a rectangular region of interest (ROI) of 85.8 mm2 placed across the middle of the fusion site between, but not inclusive of, the transverse processes, and along the central axis of the fusion mass. Areas of new bone and residual implant were calculated based on validated color pixel parameters.

The 1 day images showed the defect margins and presence of the implant materials with no adverse reactions. At 6 weeks, the bone graft of the present disclosure demonstrated significantly greater bone area (25 vs. 21 mm2; $p<0.05$), and significantly lesser implant area (15 vs. 19 mm2; $p<0.05$) than the comparative group.

The greater bone area measured in the bone graft of the present disclosure is likely due to the dissolution and bioactive response elicited by the bioactive glass component and the gradual remodeling properties of the biphasic granules. The lesser residual implant area measured in the bone graft of the present disclosure is likely due to rapid dissolution and remodeling of the bioactive glass component and the solubility of the $\beta$-TCP portion of the biphasic mineral component, compared to the limited resorption capability of the HA-based comparative material.

Figure 7:
FIG. 7 is a histology slide of HA-based Actifuse ABX from a rabbit posterolateral spine fusion study demonstrating an absence of new bone spanning the transverse processes at 12 weeks.
Figure 8:
FIG. 8 is a histology slide of 45S5 bioactive glass used alone from a rabbit posterolateral spine fusion study demonstrating an absence of new bone spanning the transverse processes at 14 weeks.
Figure 9A:
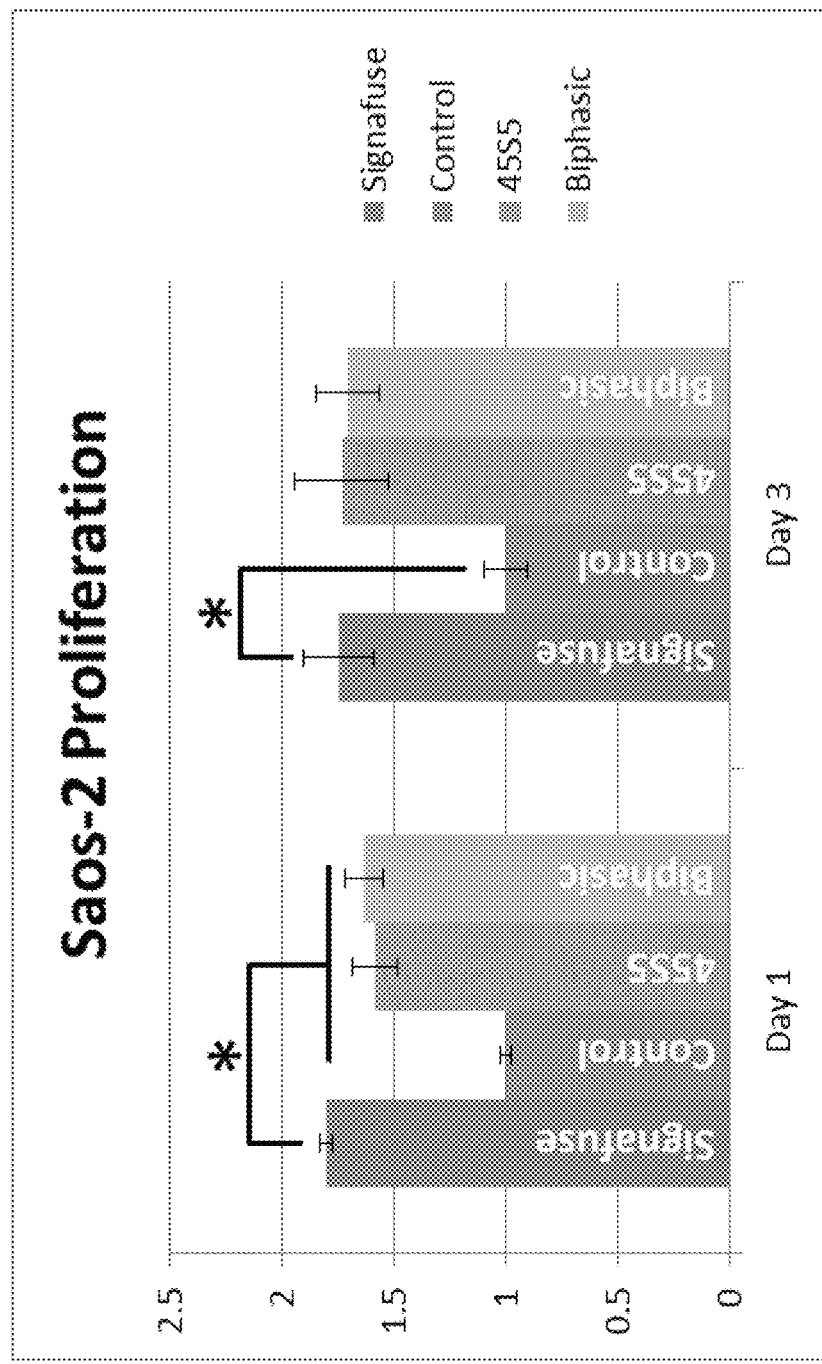
FIG. 9A illustrates that the moldable bone graft compositions taught herein lead to Saos-2 cell proliferation that is significantly increased when compared to the control at both 1 and 3 day time points. Proliferation was also increased with respect to 45S5 Bioactive Glass as well as the Biphasic granule, but only significantly at day 1
Figure 9B:
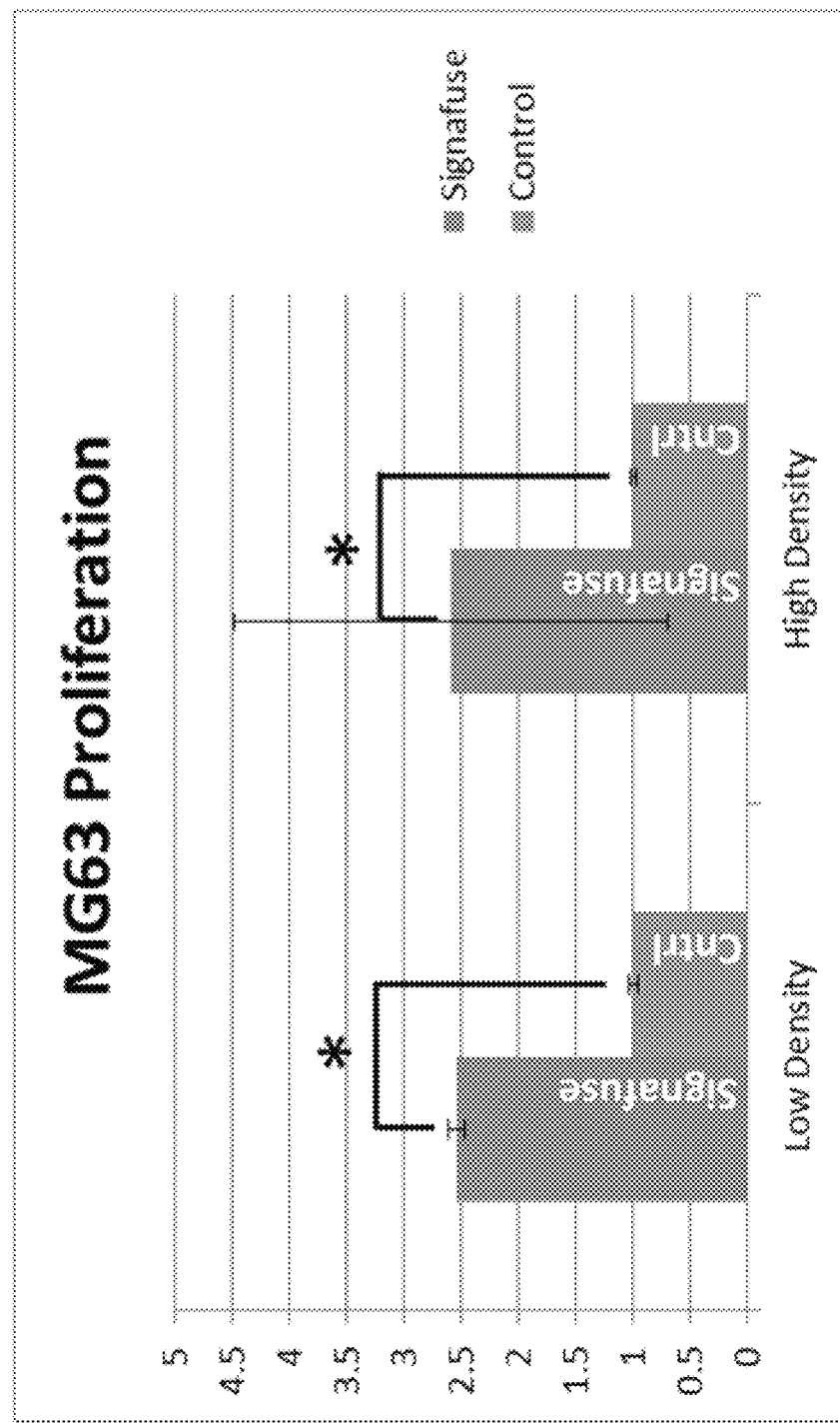
FIG. 9B illustrates that the moldable bone graft compositions taught herein lead to significantly increased cell proliferation in the MG63 cell line at 3 days, in two different seeding densities.
Figure 9C:
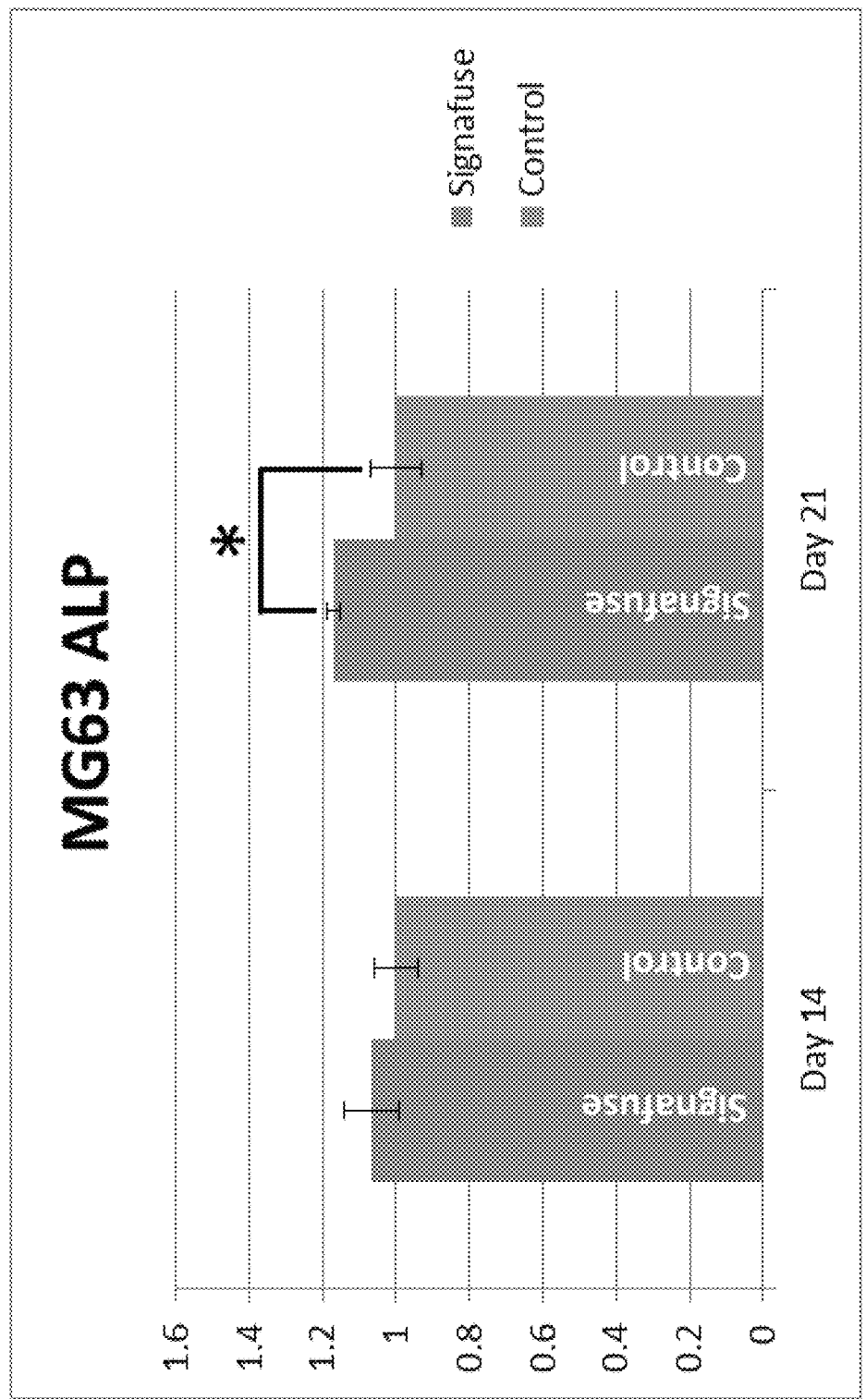
FIG. 9C illustrates that in the differentiation assay both MG63 and C2C12 cell lines were cultured with or without the presence of conditioned media. It was shown that MG63 cells upregulated ALP activity, a sign of osteoblast differentiation, at 14 and 21 days, although only statistically significantly so at 21 days.
Figure 9D:
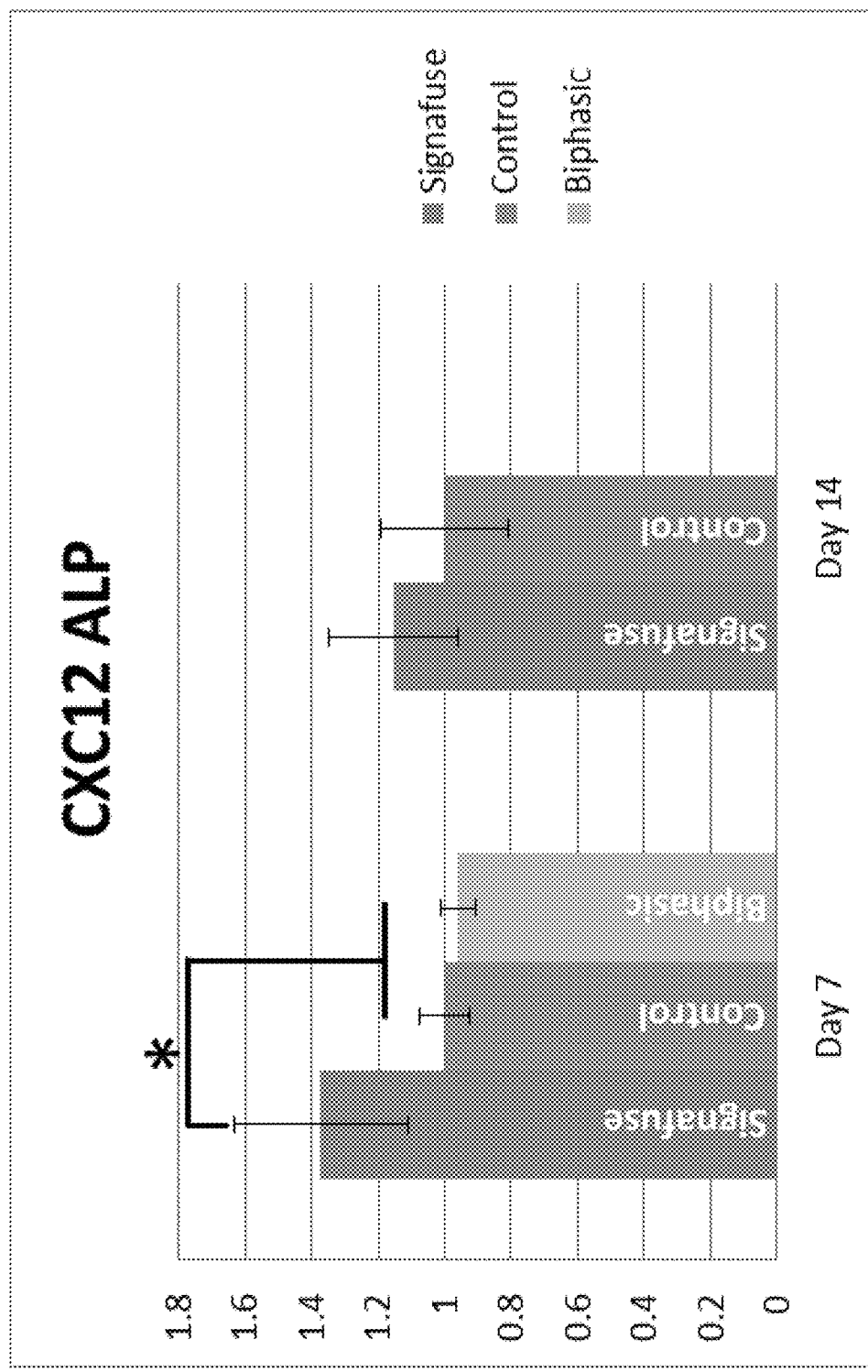
FIG. 9D illustrates that in the differentiation assay both MG63 and C2C12 cell lines were cultured with or without the presence of conditioned media. It was shown that the C2C12 cell line showed statistically significant ALP upregulation at 7 days, in comparison to both the control and the biphasic mineral and an increase compared to control at day 14, but that increase was not significant. ALP levels were quantified in the cell lysate and normalized to protein levels in each condition.

At 12 weeks, there were no statistical differences between the groups for either new bone or residual implant areas. However, although the overall morphometric area for bone was similar between groups at 12 weeks, differences in the physical structure of the remodeling bone and overall progression of defect healing were observed between the test groups. As remodeling progresses, bone will condense and align directionally according to stress across the defect. For example, the bone graft of the present disclosure demonstrated more condensed and aligned mature bone spanning between TPs, with developed marrow spaces throughout the material and defect in most animals. Conversely, the comparative group demonstrated a progression of less condensed immature bone from the margins of the TPs with less developed marrow spaces. New bone formation was not observed spanning the TPs in most animals in the comparative group as shown in FIG. 7.

Also of significant note, in a prior study by this group using the same animal model, 45S5 bioactive glass used alone was demonstrated to lack new bone formation spanning the TPs in all animals.

Example 8

Osteostimulatory Effects

The osteostimulatory effect of the present moldable bone graft composition was evaluated using the currently accepted definition of increasing osteoblast-like cell proliferation and differentiation towards a more osteoblastic fate. See, e.g. FIG. 9.

In the proliferation assay both MG63 and Saos-2 osteoblast-like cell lines were cultured with or without the presence of conditioned media. This media was created by first weighing out about 1 g of material for every 100 ml of media for a 1% solution. The material was washed with PBS twice for 20 min. The material was then equilibrated in DMEM at 37° C. for 24 hours. The solutions were pH adjusted to 7.4 and then filtered through a 0.22 µm sterile filter.

It was shown that Saos-2 cell proliferation was significantly increased when cultured in the conditioned media with respect to the control at both 1 and 3 day time points. Proliferation was also increased with respect to 45S5 Bioactive Glass as well as the Biphasic granule, but only significantly at day 1. The MG63 cell line also showed a statistically significant increase in proliferation measured at 3 days in two different seeding densities. Proliferation was quantified used an MTT assay.

In the differentiation assay both MG63 and C2C12 cell lines were cultured with or without the presence of conditioned media created by the method earlier explained. It was shown that MG63 cells upregulated ALP activity, a sign of osteoblast differentiation, at 14 and 21 days although only statistically significantly so at 21 days. The C2C12 cell line showed statistically significant ALP upregulation at 7 days in comparison to both the control and the biphasic mineral and an increase compared to control at day 14, but that increase was not significant. ALP levels were quantified in the cell lysate and normalized to protein levels in each condition.

Example 9

Anti-Microbial Effectiveness

The antimicrobial properties of the present moldable bone graft composition were evaluated by performing the USP 51 Antimicrobial Effectiveness Test.

To measure the antimicrobial properties of the device a solution of 1 g of material to 1 ml of simulated body fluid (the same as cited in example 5) is inoculated with $1 \times 10^5$ to $1 \times 10^6$ Colony Forming Units. After 1, 7, 14, and 28 days the samples are assayed for their total colony forming units.

Figure 10:
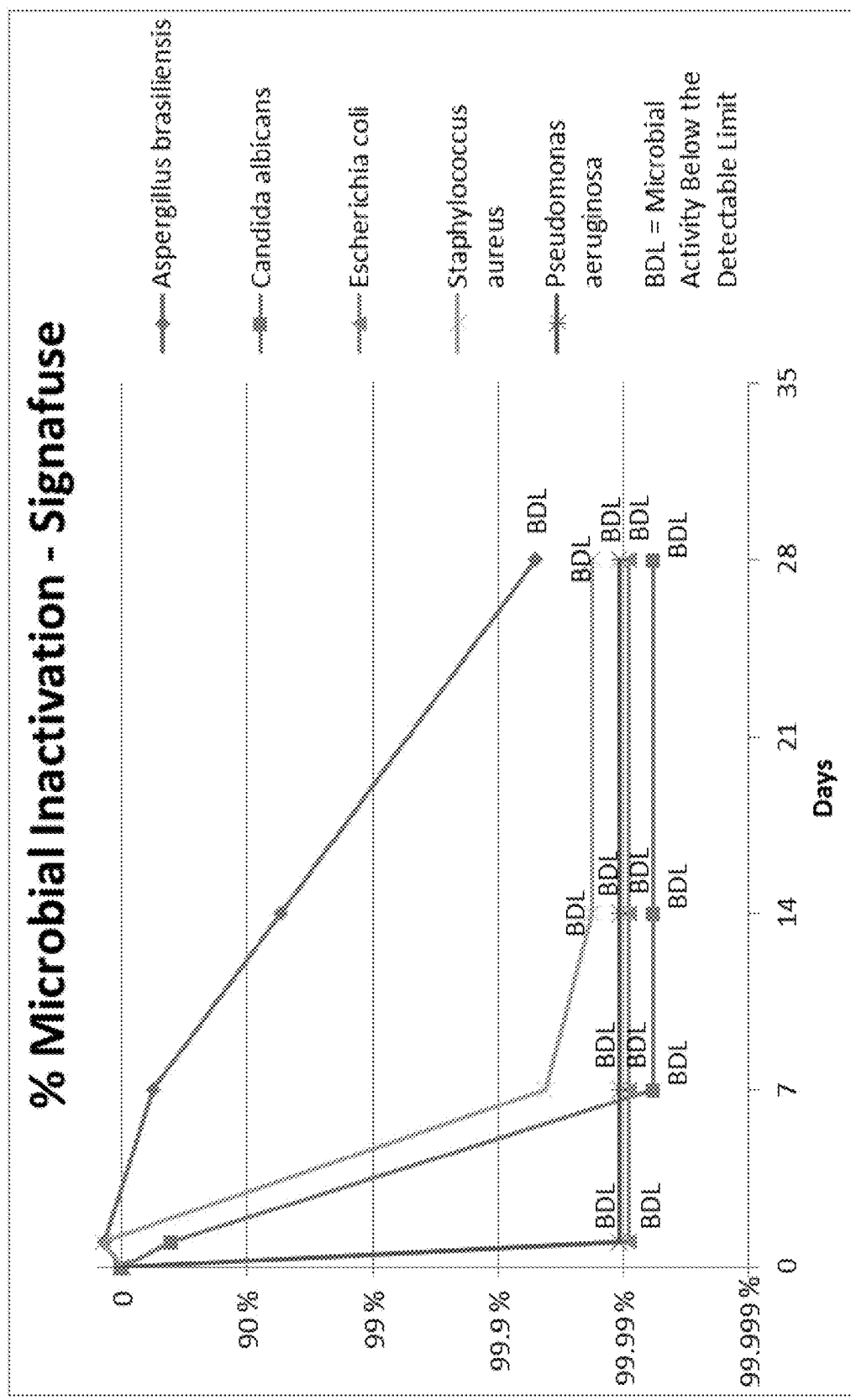
FIG. 10 illustrates that bone graft compositions of the disclosure decreased the colony forming units of all organisms throughout the course of the study, satisfying the category 1 acceptance criteria of USP 51.

The bone graft decreased the colony forming units of all organisms throughout the course of the study satisfying the category 1 acceptance criteria of USP 51. See, e.g. FIG. 10.

Although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein.

Thus, the breadth and scope of the disclosure should not be limited by any of the above-described embodiments, but should be defined only in accordance with the following claims and their equivalents. The previous description of the embodiments is provided to enable any person skilled in the art to make or use the disclosure. While the disclosure has been particularly shown and described with reference to embodiments thereof, it will be understood by those skilled in the art that various changes in form and details may be made therein without departing from the spirit and scope of the disclosure.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment, or any form of suggestion, that they constitute valid prior art or form part of the common general knowledge in any country in the world.

What is claimed is:
1. A moldable bone graft composition, comprising:
  a) about 40-80% by weight of one or more bioresorbable polymers;
  b) about 10-50% by weight of biphasic calcium phosphate particles comprising hydroxyapatite and tricalcium phosphate; and
  c) about 1-40% by weight of at least one bioactive glass, wherein said biphasic calcium phosphate particles and said bioactive glass together comprise about 20-60% by weight of the moldable bone graft composition.
2. The moldable bone graft composition of claim 1, wherein the one or more bioresorbable polymers comprise a polyalkylene oxide polymer having at least one of the following: a molecular weight of about 500-1500 grams/mole; a specific gravity of about 1.0-1.3 (at 25° C.); a viscosity of about 10-40 cSt (at 210° C.); or a melting temperature of about 38-50° C.
3. The moldable bone graft composition of claim 1, wherein the biphasic calcium phosphate particles comprise about 20-60% hydroxyapatite and about 40-80% tricalcium phosphate.
4. The moldable bone graft composition of claim 1, wherein the biphasic calcium phosphate particles have interconnected macro- and microporosity.
5. The moldable bone graft composition of claim 1, wherein about 30-90% of the biphasic calcium phosphate particles have a particle size of about 1000-2000 µm; about 10-70% of the biphasic calcium phosphate particles have a particle size of about 425-1000 µm, about 10-50% of the biphasic calcium phosphate particles have a particle size of about 710-1000 µm; and about 1-30% of the biphasic calcium phosphate particles have a particle size of about 425-710 µm.
6. The moldable bone graft composition of claim 1, wherein the bioactive glass comprises 45S5 bioactive glass.
7. The moldable bone graft composition of claim 1, wherein the bioactive glass is in the form of particles having a particle size of about 1-600 µm.
8. The moldable bone graft composition of claim 1, wherein the bioactive glass is in the form of particles having a particle size of about 1-425 µm.
9. The moldable bone graft composition of claim 1, wherein at least 80% of the bioactive glass is in the form of particles having a particle size of about 212-425 µm.
10. The moldable bone graft composition of claim 1, wherein the bioactive glass is in the form of irregular granules.
11. The moldable bone graft composition of claim 1, wherein the bioactive glass is in the form of approximately spherical particles.
12. The moldable bone graft composition of claim 1, wherein the bioactive glass is in the form of fibers.
13. The moldable bone graft composition of claim 1, wherein about 60-90% of the biphasic calcium phosphate particles and bioactive glass together are in the form of particles having a particle size of about 425-2000 µm, and about 10-40% of the particles have a particle size of about 1-425 µm.
14. A single use moldable bone graft composition of claim 1, having a mass of about 1.5-30 grams.
15. A single use moldable bone graft composition of claim 1, having a volume of about 1-20 cc.
16. The moldable bone graft composition of claim 1, having a density of about 1.2-1.8 g/cc.
17. The moldable bone graft composition of claim 1, in the form of a cylinder.
18. The moldable bone graft composition of claim 17, wherein said composition has a crush resistance force of less than about 20 lbf.
19. The moldable bone graft composition of claim 17, wherein said composition can be molded into any desired shape without loss of homogeneity.
20. The moldable bone graft composition of claim 1, having a cubical shape.
21. A syringe applicator filled with the moldable bone graft composition of claim 1.
22. The syringe applicator of claim 21, wherein the force required to eject the moldable bone graft composition from the syringe applicator is less than 20 lbf.
23. The moldable bone graft composition of claim 1, further comprising: a melt skin layer disposed on the outer surface of the composition, wherein the melt skin layer comprises the bioresorbable polymer.
24. The moldable bone graft composition of claim 1, wherein the bioresorbable polymer dissolves in PBS at 37° C. at a rate of about 0.01-0.20 grams/minute.
25. The moldable bone graft composition of claim 1, wherein the bioresorbable polymer dissolves in PBS at 37° C. in about 60-600 minutes.
26. The moldable bone graft composition of claim 1, wherein the bioresorbable polymer dissolves in PBS at 37° C. in less than 60 minutes.
27. The moldable bone graft composition of claim 1, wherein the composition is supplied with, or used in conjunction with, allograft tissue.
28. A moldable bone graft composition, comprising:
  a) about 50-70% by weight of one or more bioresorbable polymers;
  b) about 25-40% by weight of biphasic calcium phosphate particles comprising a mixture of hydroxyapatite and tricalcium phosphate; and
  c) about 1-15% by weight of at least one bioactive glass, wherein said biphasic calcium phosphate particles and said bioactive glass together comprise about 30-50% by weight of the moldable bone graft composition.
29. The moldable bone graft composition of claim 28, wherein the moldable bone graft composition forms a hydroxyapatite surface layer in simulated body fluid.
30. The moldable bone graft composition of claim 28, wherein the moldable bone graft composition stimulates mesenchymal stem cell differentiation in a cell culture assay.

31. The moldable bone graft composition of claim 28, wherein the moldable bone graft composition stimulates osteoblast cell proliferation in a cell culture assay.

32. The moldable bone graft composition of claim 28, wherein the moldable bone graft composition demonstrates an antimicrobial efficacy according to methods based on USP <51>.

33. The moldable bone graft composition of claim 28, wherein the moldable bone graft composition stimulates mesenchymal stem cell differentiation and osteoblast cell proliferation in a cell culture assay and demonstrates an antimicrobial effect.

34. The moldable bone graft composition of claim 28, wherein the moldable bone graft composition provides a spine fusion rate of greater than or equal to 50% in a New Zealand white rabbit spine fusion model.

35. A method for repairing a bone defect, comprising: applying the moldable bone graft composition of claim 1 to a bone defect in a patient in need thereof.

36. A method for repairing a bone defect, comprising: applying the moldable bone graft composition of claim 28 to a bone defect in a patient in need thereof.

37. The method of claim 35, wherein the bone defect is a spinal bone defect.

38. The method of claim 35, wherein the bone defect is in the posterolateral gutter of a vertebral body.

39. The method of claim 36, wherein the bone defect is a spinal bone defect.

40. The method of claim 36, wherein the bone defect is in the posterolateral gutter of a vertebral body.

41. The moldable bone graft composition of claim 28, further comprising: allograft tissue.

42. A moldable bone graft composition, comprising:
a) 60%±10% by weight of one or more bioresorbable polyethylene glycol polymers;
b) 30%±10% by weight of biphasic calcium phosphate particles comprising hydroxyapatite and β-tricalcium phosphate; and
c) 10%±10% by weight of at least one bioactive glass.

43. The moldable bone graft composition of claim 42, wherein the one or more bioresorbable polyethylene glycol polymers is present at 60% by weight, the biphasic calcium phosphate particles are present at 32% by weight and comprise a hydroxyapatite to β-tricalcium phosphate ratio of 60:40, and the at least one bioactive glass is present at 8% by weight.

44. The moldable bone graft composition of claim 43, wherein the one or more bioresorbable polyethylene glycol polymers comprise 48% of polyethylene glycol 1450 and 12% of polyethylene glycol 400.

45. The moldable bone graft composition of claim 43, wherein 60%±5% of the biphasic calcium phosphate particles have a particle size from 1000-2000 μm, and 30%±5% of the biphasic calcium phosphate particles have a particle size from 710-1000 μm, and 10%±5% of the biphasic calcium phosphate particles have a particle size from 425-710 μm.

46. The moldable bone graft composition of claim 43, wherein 63% of the biphasic calcium phosphate particles have a particle size from 1000-2000 μm, and 27% of the biphasic calcium phosphate particles have a particle size from 710-1000 μm, and 9% of the biphasic calcium phosphate particles have a particle size from 425-710 μm.

47. The moldable bone graft composition of claim 43, wherein 92% of the at least one bioactive glass is in the form of particles having a particle size from 212-425 μm.

48. The moldable bone graft composition of claim 42, further comprising: allograft tissue.

* * * * *